US006693063B2

(12) United States Patent
Schnabel et al.

(10) Patent No.: US 6,693,063 B2
(45) Date of Patent: Feb. 17, 2004

(54) HERBICIDAL COMPOSITION

(75) Inventors: Gerhard Schnabel, Elsenfeld (DE);
Jean Kocur, Hofheim (DE);
Hans-Peter Krause, Hofheim (DE);
Julio Martinez de Una, Liederbach (DE); Hans Philipp Huff, Eppstein (DE); Udo Bickers, Wietmarschen (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 10/023,323

(22) Filed: Dec. 18, 2001

(65) Prior Publication Data

US 2002/0115569 A1 Aug. 22, 2002

(30) Foreign Application Priority Data

Dec. 20, 2000 (DE) .......................... 100 63 960

(51) Int. Cl.$^7$ .................... A01N 25/28; A01N 37/34
(52) U.S. Cl. ....................... 504/310; 504/359
(58) Field of Search ................... 504/310, 359

(56) References Cited

U.S. PATENT DOCUMENTS

| 5,021,083 A | 6/1991 | Schapira et al. ............... 71/105 |
| 5,074,905 A | 12/1991 | Frisch et al. .................. 71/120 |
| 6,093,681 A | 7/2000 | Ward et al. .................. 504/116 |
| 6,291,401 B1 | 9/2001 | Dufau et al. ................. 504/363 |

FOREIGN PATENT DOCUMENTS

| CA | 2 093 377 | 10/1994 |
| DE | 268 147 A1 | 5/1989 |
| EP | 0 228 943 | 7/1987 |
| EP | 0 306 376 | 3/1989 |
| EP | 0 261 492 A2 | 3/1998 |
| EP | 0 968 649 | 1/2000 |
| WO | WO 98/31223 | 7/1998 |
| WO | WO 99/55155 | 11/1999 |
| WO | WO 00/51427 | 9/2000 |
| WO | WO 00/64258 | 11/2000 |
| WO | WO 01/50861 | 7/2001 |
| WO | WO 01/76368 A1 | 10/2001 |

OTHER PUBLICATIONS

C.D.S. Tomlin "The Pesticide Manual", 12$^{th}$ edition (1999). The British Crop Protection Council, (ISBN 19 01 39 61 26); p. 110ff and 548ff.
Database WPI, AN 1989–273339, also referred to as XP 002196614 and JP 01 197403 A1 published Aug. 9, 1989.

*Primary Examiner*—S. Mark Clardy
(74) *Attorney, Agent, or Firm*—Frommer Lawrence & Haug LLP

(57) ABSTRACT

The present invention relates to a herbicidal composition, comprising

A) one or more compounds of the formula (I)

$$\text{Hal}^1\text{—C}_6\text{H}_2(\text{OR}^1)(\text{CN})\text{—Hal}^2 \quad (I)$$

in which
Hal$^1$ and Hal$^2$ are identical or different halogen atoms, R$^1$ is H, a cation or a C$_1$–C$_{20}$-carbon-containing radical and B) one or more surfactants, comprising as structural element at least 12 alkylene oxide units.

9 Claims, No Drawings

HERBICIDAL COMPOSITION

The present invention relates to the field of chemical crop protection, in particular to combinations of specific herbicides of the hydroxybenzonitrile type with specific surfactants.

Herbicides of the hydroxybenzonitrile type, such as ioxynil or bromoxynil and derivatives thereof, such as salts or esters, are suitable for controlling undesirable vegetation, for example in crops such as corn or wheat.

It is also known that the abovementioned herbicidal compounds can be combined with surfactants for preparing standard formulations.

It was an object of the present invention to provide herbicidal compositions with particularly high herbicidal activity.

Surprisingly, it has now been found that this object is achieved by herbicidal compositions comprising herbicides of the hydroxybenzonitrile type of the formula (I) from below in combination with specific surfactants.

Accordingly, the present invention relates to herbicidal compositions, comprising
A) one or more compounds of the formula (I)

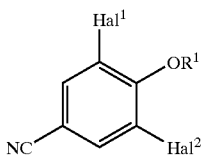

(I)

in which
Hal$^1$ and Hal$^2$ are identical or different halogen atoms such as F, Cl, Br, I, preferably Br or I, and
R$^1$ is H, a cation or a C$_1$–C$_{20}$-carbon-containing radical, and
B) one or more surfactants, comprising as structural elements at least 12 alkylene oxide units, preferably 12–200 alkylene oxide units.

Preferred compounds of the formula (I) are compounds in which R$^1$ is H, a C$_1$–C$_{20}$-carbon-containing radical, for example a C$_1$–C$_{20}$-acyl radical, or a cation such as an ammonium ion, for example $^\oplus$NH$_4$, $^\oplus$NH$_3$CH$_2$CH$_2$OH, $^\oplus$NH$_2$(CH$_2$CH$_2$OH)$_2$, $^\oplus$NH(CH$_2$CH$_2$OH)$_3$, $^\oplus$N(CH$_2$CH$_2$OH)$_4$, $^\oplus$NH$_3$(C$_1$–C$_{18}$)-alkyl, $^\oplus$NH$_2$[(C$_1$–C$_{18}$)-alkyl]$_2$, $^\oplus$NH[(C—C$_{18}$)-alkyl]$_3$ or $^\oplus$N[(C$_1$–C$_{18}$)-alkyl]$_4$, a sulfonium ion, for example $^\oplus$S[(C$_1$–C$_6$)-alkyl]$_3$, a phosphonium ion, for example $^\oplus$P[(C$_1$–C$_6$)-alkyl]$_4$, an alkali metal ion, for example Na$^\oplus$ or K$^\oplus$, or an alkaline earth metal ion, for example ½ Ca$^{2\oplus}$, or ½ Mg$^{2\oplus}$, or a transition group metal ion, for example, ½ Zn$^{2\oplus}$.

A C$_1$–C$_{20}$-carbon-containing radical R$^1$ can be unsubstituted or substituted, linear, branched or cyclic, saturated or unsaturated, aliphatic or (hetero)aromatic. Suitable substituents are, for example, one or more radicals from the group consisting of oxo, (=O), OH, (C$_1$–C$_6$)-(halo)alkyl or halogen (F, Cl, Br, I). R$^1$ is preferably a carbon-containing acyl radical, such as (C$_1$–C$_{19}$)-alkylcarbonyl, preferably (C$_1$–C$_{10}$)-alkylcarbonyl such as propylcarbonyl (butyrate), hexylcarbonyl (heptanoate) or heptylcarbonyl (octanoate).

Preference is furthermore given to compounds of the formula (I) in which Hal$^1$ and Hal$^2$ are identical halogen atoms, in particular Br or I.

The formula (I) also embraces all stereoisomers having the same topological attachment of the atoms, and mixtures thereof. Such compounds contain one or more asymmetrically substituted carbon atoms or else double bonds which are not specifically shown in the general formulae. The possible stereoisomers, such as enantiomers, diastereomers, Z and E isomers and tautomers, defined by their specific spatial form, can be obtained by customary methods from mixtures of the stereoisomers or else be prepared by stereoselective reactions in combination with the use of stereochemically pure starting materials.

Compounds of the formula (I) are known, for example, from C. D. S. Tomlin, "The Pesticide Manual", 12th edition (1999), The British Crop Protection Council, (ISBN 19 01 39 61 26); p. 110ff and p. 548ff.

Particularly preferred compounds of the formula (I) are, for example, bromoxynil (A1) and ioxynil (A5) and their salts and esters, such as bromoxynil-sodium (A2), bromoxynil-potassium (A3), bromoxynil-heptylcarbonyl (=bromoxynil-octanoate) (A4), ioxynil-sodium (A6), ioxynil-potassium (A7), ioxynil-heptylcarbonyl (=ioxynil-octanoate) (A8), bromoxynil-hexylcarbonyl (=bromoxynil-heptanoate) (A9), bromoxynil-propylcarbonyl (=bromoxynil-butyrate) (A10), ioxynil-hexylcarbonyl (=ioxynil-heptanoate) (A11) and ioxynil-propylcarbonyl (=ioxynil-butyrate) (A12) and mixtures thereof.

The surfactant B) preferably contains 12–200 alkylene oxide units, one or more C$_1$–C$_{40}$-carbon-containing radicals and, if appropriate, one or more polar functional groups.

The term "alkylene oxide units" is preferably to be understood as meaning units of C$_2$–C$_{10}$-alkylene oxides, such as ethylene oxide, propylene oxide, butylene oxide or hexylene oxide, where the units within the surfactant may be identical or different from one another.

Suitable polar functional groups are, for example, anionic groups such as carboxylate, carbonate, sulfate, sulfonate, phosphate or phosphonate, cationic groups such as groups having a cationic nitrogen atom, for example a pyridinium group or an —NR$^Y_3$ group, where R$^Y$ are identical or different radicals from the group consisting of H and unsubstituted or substituted C$_1$–C$_{10}$-hydrocarbon radicals such as (C$_1$–C$_{10}$)-alkyl, electrically neutral polar groups, such as carbonyl, imine, cyano or sulfonyl, or betainic groups, such as

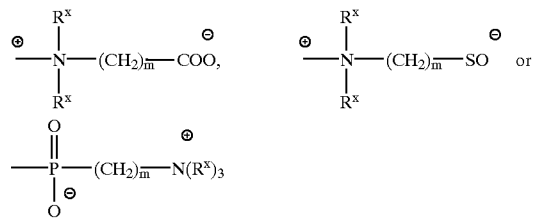

in which m=1, 2, 3, 4 or 5 and R$^X$ are identical or different unsubstituted or substituted C$_1$–C$_{10}$-hydrocarbon radicals such as (C$_1$–C$_{10}$)-alkyl.

As component B), the composition according to the invention preferably comprises one or more surfactants of the formula (II)

$$R^r\text{—}(EO)_x(PO)_y(EO)_z\text{—}R^b \tag{II}$$

in which
EO is an ethylene oxide unit,
PO is a propylene oxide unit,
x is an integer from 0 to 50, preferably from 1 to 50,
y is an integer from 0 to 50,
z is an integer from 0 to 50,
where the sum (x+y+z)≧12 and ≦150, and $R^\delta$ is OH, an unsubstituted or substituted $C_1-C_{40}$-hydrocarbonoxy radical, an O-acyl radical, such as O—CO$R^I$, O—CO—O$R^I$, O—CO—N$R^I R^{II}$, O—P(O)($R^1$)[(EO)$_u$(O$R^{II}$)] or O—P(O)[(EO)$_u$(O$R^I$)][(EO)$_v$(O$R^{II}$)], or N$R^I R^{II}$ or [N$R^I R^{II} R^{III}$]$^\oplus$X$^\ominus$, where $R^I$, $R^{II}$ and $R^{III}$ are identical or different and are H or an unsubstituted or substituted $C_1-C_{30}$-hydrocarbon radical which may be attached via a group (EO)$_w$ where w is an integer from 1 to 50, and where X$^\ominus$ is an anion (for example the anion of an inorganic acid such as a carboxylic acid anion, for example acetate or lactate, or the anion of an inorganic acid, such as ½ sulfate, [O—SO$_3$—CH$_3$]$^\ominus$, sulfonate, ⅓ phosphate, phosphonate or halide, such as Cl$^\ominus$ or Br$^\ominus$), and u and v, independently of one another, are integers from 0 to 50, and $R^\delta$ is H, an unsubstituted or substituted $C_1-C_{40}$-hydrocarbon radical, an acyl radical, such as CO$R^I$, CO—O$R^I$, CO—N$R^I R^{II}$, P(O)($R^I$)[(EO)$_u$(O$R^{II}$)] or P(O)[(EO)$_u$(O$R^I$)][(EO)$_v$(O$R^{II}$)], or N$R^I R^{II}$ or [N$R^I R^{II} R^{III}$]$^\oplus$X$^\ominus$, where $R^I$, $R^{II}$ and $R^{III}$ are identical or different and are H or an unsubstituted or substituted $C_1-C_{30}$-hydrocarbon radical which may be attached via a group (EO)$_w$ where w is an integer from 1 to 50, and where X$^\ominus$ is an anion (for example the anion of an organic acid such as a carboxylic acid anion, for example acetate or lactate, or the anion of an inorganic acid, such as ½ sulfate, [O—SO$_3$—CH$_3$]$^\ominus$, sulfonate, ⅓ phosphate, phosphonate or halide, such as Cl$^\ominus$ or Br$^\ominus$), and u and v, independently of one another, are integers from 0 to 50.

The abbreviations EO and PO in formula (II) denote an ethylene oxide unit and a propylene oxide unit, respectively, also when used elsewhere in the description.

Preference is given to surfactants of the formula (II), in which the sum (x+y+z)$\geq$12 and $\leq$150, preferably 12–100, particularly preferably 12–80, and $R^\gamma$ is OH, an unsubstituted or substituted $C_1-C_{30}$-hydrocarbonoxy radical, preferably a $C_4-C_{30}$-hydrocarbonoxy radical, such as a $C_8$-, $C_{10}$-, $C_{12}$-, $C_{13}$- (for example isotridecyl-), $C_{14}$-, $C_{16}$-, $C_{18}$-, $C_{20}$-alkoxy radical, -alkenyloxy radical or -alkynyloxy radical, or an unsubstituted or substituted $C_6-C_{14}$-aryloxy radical, for example a $C_6-C_{14}$-aryloxy radical which is mono- or polysubstituted by ($C_1-C_{20}$)-alkyl or ($C_7-C_{20}$)-arylalkyl such as styryl, such as p-octylphenoxy, p-nonylphenoxy, 2,4-dibutylphenoxy, 2,4,6-triisobutylphenoxy, 2,4,6-tri-n-butylphenoxy, 2,4,6-tri-sec-butylphenoxy or mono-, di- or tristyrylphenyl, or $R^\gamma$ is O—CO—$R^I$, O—COO$R^I$, N$R^I R^{II}$ or [N$R^I R^{II} R^{III}$]$^\oplus$X$^\ominus$, where $R^I$, $R^{II}$ and $R^{III}$ are identical or different and are H, an unsubstituted or substituted $C_1-C_{30}$-hydrocarbon radical, preferably a $C_4-C_{20}$-hydrocarbon radical, such as a $C_8$-, $C_{10}$-, $C_{12}$-, $C_{13}$- (for example isotridecyl-), $C_{14}$-, $C_{16}$-, $C_{18}$-, $C_{20}$-alkyl radical, -alkenyl radical or -alkynyl radical or an unsubstituted or substituted $C_6-C_{14}$-aryl radical, for example a $C_6-C_{14}$-aryl radical which is mono- or polysubstituted by ($C_1-C_{20}$)-alkyl or ($C_7-C_{20}$)-arylalkyl such as styryl, such as p-octylphenyl, p-nonylphenyl, 2,4-dibutylphenyl, 2,4, 6-triiso-butylphenyl, 2,4,6-tri-n-butylphenyl, 2,4,6-tri-sec-butylphenyl or mono-, di- or tristyrylphenyl, or $R^I$, $R^{II}$ and $R^{III}$ are identical or different (EO)$_w$—$R^{IV}$, where $R^{IV}$ is H or an unsubstituted or substituted $C_1-C_{20}$-hydrocarbon radical, such as a $C_8$-, $C_{10}$-, $C_{12}$-, $C_{13}$- (for example isotridecyl-), $C_{14}$-, $C_{16}$-, $C_{18}$-, $C_{20}$-alkyl radical, -alkenyl radical or -alkynyl radical, or an unsubstituted or substituted $C_6-C_{14}$-aryl radical, for example a $C_6-C_{14}$-aryl radical which is mono- or poly-substituted by ($C_1-C_{20}$)-alkyl or ($C_7-C_{20}$)-arylalkyl such as styryl, such as p-octylphenyl, p-nonylphenyl, 2,4-dibutylphenyl, 2,4,6-triisobutylphenyl, 2,4,6-tri-n-butylphenyl, 2,4,6-tri-sec-butylphenyl or mono-, di- or tristyrylphenyl, and w is an integer from 1 to 50, and X$^\ominus$ is an anion, and $R^\delta$ is H, an unsubstituted or substituted $C_1-C_{30}$-hydrocarbon radical, preferably a $C_1-C_{20}$-hydrocarbon radical such as a $C_1$-, $C_2$-, $C_3$-, $C_4$-, $C_5$-, $C_6$-, $C_8$-, $C_{10}$-, $C_{12}$-, $C_{13}$- (for example isotridecyl-), $C_{14}$-, $C_{16}$-, $C_{18}$-, $C_{20}$-alkyl radical, -alkenyl radical or -alkynyl radical, or an unsubstituted or substituted $C_6-C_{14}$-aryl radical, for example a $C_6-C_{14}$-aryl radical which is mono- or polysubstituted by ($C_1-C_{20}$)-alkyl or ($C_7-C_{20}$)-arylalkyl such as styryl, such as p-octylphenyl, p-nonylphenyl, 2,4-dibutylphenyl, 2,4,6-triisobutylphenyl, 2,4,6-tri-n-butylphenyl, 2,4,6-tri-sec-butylphenyl or mono-, di- or tristyrylphenyl, or $R^\delta$ is CO—$R^I$, COO$R^I$, N$R^{II} R^{III}$ or [N$R^I R^{II} R^{III}$]$^\oplus$X$^\ominus$, where $R^I$, $R^{II}$ and $R^{III}$ are identical or different substituents from the group consisting of H, an unsubstituted or substituted $C_1-C_{30}$-hydrocarbon radical, such as a $C_1$-, $C_2$-, $C_3$-, $C_4$-, $C_5$-, $C_6$-, $C_8$-, $C_{10}$-, $C_{12}$-, $C_{13}$- (for example isotridecyl-), $C_{14}$-, $C_{16}$-, $C_{18}$-, $C_{20}$-alkyl radical, -alkenyl radical or -alkynyl radical, or an unsubstituted or substituted $C_6-C_{14}$-aryl radical, for example a $C_6-C_{14}$-aryl radical which is mono- or poly-substituted by ($C_1-C_{20}$)-alkyl or ($C_7-C_{20}$)-arylalkyl such as styryl, such as p-octylphenyl, p-nonylphenyl, 2,4-dibutylphenyl, 2,4,6-triisobutylphenyl, 2,4,6-tri-n-butylphenyl, 2,4,6-tri-sec-butylphenyl or mono-, di- or tristyrylphenyl, or $R^I$, $R^{II}$ and $R^{III}$ are identical or different (EO)$_w$—$R^{IV}$, where $R^{IV}$ is H or an unsubstituted or substituted $C_1-C_{30}$-hydrocarbon radical, preferably $C_1-C_{20}$-hydrocarbon radical, such as a $C_1$-, $C_2$-, $C_3$-, $C_4$-, $C_5$-, $C_6$-, $C_8$-, $C_{10}$-, $C_{12}$-, $C_{13}$- (for example isotridecyl-), $C_{14}$-, $C_{16}$-, $C_{18}$-, $C_{20}$-alkyl radical, -alkenyl radical or -alkynyl radical, or an unsubstituted or substituted $C_6-C_{14}$-aryl radical, for example a $C_6-C_{14}$-aryl radical which is mono- or polysubstituted by ($C_1-C_{20}$)-alkyl or ($C_7-C_{20}$)-arylalkyl such as styryl, such as p-octylphenyl, p-nonylphenyl, 2,4-dibutylphenyl, 2,4,6-triisobutylphenyl, 2,4,6-tri-n-butylphenyl, 2,4,6-tri-sec-butylphenyl or mono-, di- or tristyrylphenyl, and w is an integer from 1 to 50, and X$^\ominus$ is an anion.

Preferred surfactants B) are surfactants of the formulae B1–B3 below,

B1) ($C_8-C_{30}$)alkyl-O—(EO)$_x$(PO)$_y$—$R^2$

B2) ($C_8-C_{30}$)alkyl-CO—O—(EO)$_x$(PO)$_y$—CO—($C_8-C_{30}$)alkyl

B3) Ar—O—(EO)$_x$(PO)$_y$—$R^3$ where $R^2$ is H, CO—($C_1-C_{17}$)-alkyl, ($C_1-C_{18}$)-alkyl, SO$_3^\ominus$, P(O)O$_2^{2\ominus}$, [($C_8-C_{30}$)-alkyl-O-(EO)$_x$—(PO)$_4$]—P(O)—O$^\ominus$, [($C_8-C_{30}$)-alkyl-O (EO)$_x$(PO)$_4$]$_2$—P—O$^\ominus$, $R^3$ is H, CO—($C_1-C_{17}$)-alkyl, ($C_1-C_{18}$)-alkyl, SO$_3^\ominus$, P(O)O$_2^{2\ominus}$, [Ar—O—(EO)$_x$(PO)$_y$]P(O)O$^\ominus$, [Ar—O—(EO)$_x$(PO)$_y$]$_2$P(O), x is an integer from 0 to 50, y is an integer from 0 to 50 and x+y is an integer $\geq$12 and $\leq$100, and Ar is an unsubstituted or substituted aryl radical such as unsubstituted or substituted phenyl, for example. mono-, di-, tri-, tetra- or penta- ($C_1-C_{10}$)-alkylphenyl, preferably di- and tributylphenyl, such as di- and tri-n-butyl-phenyl, -sec-butylphenyl, -isobutylphenyl and -tert-butylphenyl, and also mono-, di- or tristyrylphenyl.

Particular preference is given to surfactants of the formula (II) in which the sum (x+y+z) is 15–80, preferably 20–50, $R^\gamma$ is ($C_8-C_{18}$)-alkoxy, ($C_8-C_{18}$)-alkenyloxy or ($C_8-C_{18}$)-alkynyloxy, ($C_7-C_{17}$)-alkylcarbonyloxy, ($C_7-C_{17}$)-alkenylcarbonyloxy, ($C_7-C_{17}$)-alkynylcarbonyloxy, ($C_1$–$C_{10}$)-alkylphenoxy such as octylphenoxy, p-nonylphenoxy, 2,4,6-tri-n-butylphenoxy, 2,4,6-triisobutylphenoxy or 2,4,6-tri-sec-butylphenoxy, or ($C_7$–$C_{20}$)-arylalkylphenoxy such as mono-, di- or tristyrylphenoxy, and $R^\delta$ is H, ($C_1$–$C_{18}$)-alkyl, preferably ($C_1$–$C_6$)-alkyl, ($C_2$–$C_{18}$)-alkenyl, preferably ($C_2$–$C_6$)-alkenyl, or ($C_2$–$C_{18}$)-alkynyl, preferably ($C_2$–$C_6$)-alkynyl, CO—H, CO—($C_1$–$C_{17}$)-alkyl, CO—($C_2$–$C_{17}$)-alkenyl or CO—($C_2$–$C_{17}$)-alkynyl.

Surfactants B), for example those of the formula (II), are known from the literature, for example from McCutcheon's, Emulsifiers&Detergents 1994, Vol. 1: North American Edition and Vol. 2 International Edition; McCutcheon Division, Glen Rock N.J., USA, and also from "Surfactants in Consumer Products", J. Falbe, Springer-Verlag Berlin, 1987. By way of reference, the surfactants B) mentioned are expressly incorporated into this description. Moreover, surfactants B), for example those of the formula (II), are also commercially available, for example under the trade names Genapol® X or O or T series, Sapogenat® T series, Arkopal® N series, Afilan® PTU, Hordaphos® and Emulsogen® series from Clariant AG; Agrilan® types from Akcros Organics; Alkamul® and Antarox® types from Rhodia; Emulan® types (NP, OC, OG, OK) from BASF AG; Dehydol® types from Henkel; Agent W® types from Stepan Company; Crodamel® types from Croda GmbH. By way of reference, the surfactants B) mentioned in the product brochures in question are expressly incorporated into this description.

Examples of surfactants B), for example those of the formula (II), are listed in Table 1 below:

TABLE 1

| Ex. No. | $R^\gamma$ | x | y | z | $R^\delta$ |
|---|---|---|---|---|---|
| 1 | octyl-O— | 15 | — | — | H |
| 2 | decyl-O— | 15 | — | — | H |
| 3 | " | 20 | — | — | H |
| 4 | tridecyl-O— | 15 | — | — | H |
| 5 | " | 16 | — | — | H |
| 6 | " | 17 | — | — | H |
| 7 | " | 18 | — | — | H |
| 8 | " | 19 | — | — | H |
| 9 | " | 20 | — | — | H |
| 10 | " | 25 | — | — | H |
| 11 | " | 30 | — | — | H |
| 12 | " | 15 | — | — | Me |
| 13 | " | 17 | — | — | Me |
| 14 | " | 15 | — | — | $COCH_3$ |
| 15 | " | 17 | — | — | $COCH_3$ |
| 16 | ($C_{12}$-alkyl)-O— | 15 | — | — | H |
| 17 | " | 16 | — | — | H |
| 18 | " | 17 | — | — | H |
| 19 | " | 20 | — | — | H |
| 20 | " | 15 | — | — | Me |
| 21 | " | 15 | — | — | $COCH_3$ |
| 22 | ($C_{14}$-alkyl)-O— | 15 | — | — | H |
| 23 | " | 16 | — | — | H |
| 24 | " | 17 | — | — | H |
| 25 | " | 18 | — | — | H |
| 26 | " | 19 | — | — | H |
| 27 | " | 20 | — | — | H |
| 28 | " | 25 | — | — | H |
| 29 | " | 30 | — | — | H |
| 30 | " | 40 | — | — | H |
| 31 | ($C_{16}$-alkyl)-O— | 15 | — | — | H |
| 32 | " | 20 | — | — | H |
| 33 | " | 40 | — | — | H |
| 34 | ($C_{18}$-alkyl)-O— | 15 | — | — | H |
| 35 | " | 20 | — | — | H |
| 36 | ($C_9$-alkyl)-CO—O— | 15 | — | — | Me |
| 37 | " | 16 | — | — | Me |
| 38 | " | 20 | — | — | Me |
| 39 | " | 50 | — | — | Me |
| 40 | ($C_{10}$-alkyl)-CO—O— | 15 | — | — | Me |
| 41 | " | 20 | — | — | Me |
| 42 | ($C_{11}$-alkyl)-CO—O— | 15 | — | — | Me |
| 43 | " | 16 | — | — | Me |
| 44 | " | 17 | — | — | Me |
| 45 | " | 20 | — | — | Me |
| 46 | " | 25 | — | — | Me |
| 47 | ($C_{12}$-alkyl)-CO—O— | 15 | — | — | Me |
| 48 | " | 20 | — | — | Me |
| 49 | " | 25 | — | — | Me |
| 50 | ($C_{13}$-alkyl)-CO—O— | 15 | — | — | Me |
| 51 | " | 20 | — | — | Me |
| 52 | ($C_{15}$-alkyl)-CO—O— | 15 | — | — | Me |
| 53 | " | 20 | — | — | Me |
| 54 | ($C_9$-alkyl)-CO—O— | 15 | — | — | ($C_9$-alkyl)-CO |
| 55 | " | 20 | — | — | " |
| 56 | ($C_{11}$-alkyl)-CO—O— | 15 | — | — | ($C_{11}$-alkyl)-CO |
| 57 | " | 20 | — | — | " |
| 58 | " | 30 | — | — | " |
| 59 | ($C_{12}$-alkyl)-CO—O— | 15 | — | — | ($C_{12}$-alkyl)-CO |
| 60 | " | 20 | — | — | " |
| 61 | ($C_{13}$-alkyl)-CO—O— | 20 | — | — | ($C_{13}$-alkyl)-CO |
| 62 | ($C_{15}$-alkyl)-CO—O— | 15 | — | — | ($C_{15}$-alkyl)-CO |
| 63 | isotridecyl-O— | — | 5 | 10 | H |
| 64 | " | 10 | 5 | 10 | H |
| 65 (Genamin® 0, 200 Clariant) | $C_{18}H_{35}/C_{16}H_{31}$—N—(EO)$_{10}$H | 10 | — | — | H |

Unless specifically defined otherwise, the following definitions apply in general to the radicals in the formulae for (I) and (II) and in the formulae below.

If the term "acyl radical" is used in this description, this means the radical of an organic acid which is formally generated by removing an OH group from the organic acid, for example the radical of a carboxylic acid and radicals of acids derived therefrom, such as thiocarboxylic acid, unsubstituted or N-substituted imino carboxylic acids or the radicals of carbonic acid monoesters, unsubstituted or N-substituted carbaminic acids, sulfonic acids, sulfinic acids, phosphonic acids, phosphinic acids.

Preferred acyl radicals are formyl or acyl from the group consisting of CO—$R^z$, CS—$R^z$, CO—ORZ, CS—ORZ, CS—SRZ, SORZ and $SO_2R^z$, where $R^z$ is in each case a $C_1$–$C_{10}$-hydrocarbon radical such as $C_1$–$C_{10}$-alkyl or $C_6$–$C_{10}$-aryl which is unsubstituted or substituted, for example by one or more substitutents from the group consisting of halogen, such as F, Cl, Br, I, alkoxy, haloalkoxy, hydroxyl, amino, nitro, cyano or alkylthio, or $R^z$ is aminocarbonyl or aminosulfonyl, where the two last-mentioned radicals are unsubstituted, N-monosubstituted or N,N-disubstituted, for example by substituents from the group consisting of alkyl and aryl.

Acyl is, for example, formyl, haloalkylcarbonyl, alkylcarbonyl, such as ($C_1$–$C_{10}$)-alkylcarbonyl, phenylcarbonyl, where the phenyl ring may be substituted, or alkyloxycarbonyl, such as ($C_1$–$C_4$)-alkyloxycarbonyl, phenyloxycarbonyl, benzyloxycarbonyl, alkylsulfonyl, such as ($C_1$–$C_4$)-alkylsulfonyl, alkylsulfinyl, such as ($C_1$–$C_4$)-alkylsulfinyl, N-alkyl-1-iminoalkyl, such as N-($C_1$–$C_4$)-alkyl-1-imino-($C_1$–$C_4$)-alkyl, and other radicals of organic acids.

Carbon-containing radicals are organic radicals which contain at least one carbon atom, preferably 1 to 40 carbon atoms, particularly preferably 1 to 30 carbon atoms, very particularly preferably 1 to 20 carbon atoms, and furthermore at least one atom of one or more other elements of the Periodic Table of the Elements, such as H, Si, N, P, O, S, F, Cl, Br or 1. Examples of carbon-containing radicals are unsubstituted or substituted hydrocarbon radicals which may be attached to the skeleton directly or via a heteroatom, such as Si, N, S, P or O, unsubtituted or substituted heterocyclyl radicals, which may be attached to the skeleton directly or via a heteroatom, such as Si, N, S, P or O, carbon-containing acyl radicals or cyano.

The term "heteroatom" is to be understood as meaning various elements of the Periodic Table of the Elements which are different from carbon and hydrogen, for example Si, N, S, P, O, F, Cl, Br or 1.

Hydrocarbon(oxy) radicals are straight-chain, branched or cyclic, saturated or unsaturated, aliphatic or aromatic hydrocarbon(oxy) radicals, for example alkyl, alkenyl, alkynyl, or carbocyclic rings, such as cycloalkyl, cycloalkenyl or aryl, and the hydrocarbonoxy radicals which correspond to these hydrocarbon radicals, such as alkoxy, alkenyloxy, alkynyloxy, cycloalkoxy, cycloalkenyloxy or aryloxy; here, aryl is a mono-, bi- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having 1 to 30 carbon atoms or cycloalkyl having 3, 4, 5, 6 or 7 ring atoms or phenyl.

Substituted radicals, such as substituted hydrocarbon (oxy) radicals, for example substituted alkyl, alkenyl, alkynyl, or carbocyclic rings, such as cycloalkyl, cycloalkenyl or aryl, and the hydrocarbonoxy radicals which correspond to these hydrocarbon radicals, such as alkoxy, alkenyloxy, alkynyloxy, cycloalkoxy, cycloalkenyloxy or phenoxy, or substituted heterocyclyl radicals, are, for example, a substituted radical derived from the unsubstituted skeleton, where the substituents are, for example, one or more, preferably 1, 2 or 3, radicals from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also unsubstituted or substituted alkyl, such as haloalkyl, alkoxyalkyl, haloalkoxyalkyl, alkylthioalkyl, hydroxyalkyl, aminoalkyl, nitroalkyl, carboxyalkyl, cyanoalkyl or azidoalkyl, and also the unsaturated aliphatic radicals which correspond to the saturated hydrocarbon-containing radicals mentioned, such as alkenyl, alkynyl, alkenyloxy, alkynyloxy etc. Among the radicals having carbon atoms, preference is given to those having 1 to 4 carbon atoms, in particular 1 or 2 carbon atoms. In general, preference is given to substituents from the group consisting of halogen, for example fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy and chlorine.

The carbon-containing radicals, such as alkyl, alkoxy, haloalkyl, haloalkoxy, alkylamino and alkylthio, and the corresponding unsaturated and/or substituted radicals, can in each case be straight-chain or branched in the carbon skeleton. Unless specifically indicated otherwise, among these radicals, preference is given to the lower carbon skeletons, for example those having 1 to 6 carbon atoms or, in the case of unsaturated groups, those having 2 to 6 carbon atoms. Alkyl radicals, also in the composite meanings such as alkoxy, haloalkyl, etc., are, for example, methyl, ethyl, n- or isopropyl, n-, iso-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meaning of the possible unsaturated radicals which correspond to the alkyl radicals; alkenyl is, for example, allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl; alkynyl is, for example, propargyl, but-2-in-1-yl, but-3-in-1-yl, 1-methyl-but-3-in-1-yl.

Cycloalkyl is preferably a cyclic alkyl radical having 3 to 8, preferably 3 to 7, particularly preferably 3 to 6, carbon atoms, for example cyclopropyl, cyclobutyl, cyclopentyl and cyclohexyl. Cycloalkenyl and cycloalkynyl denote the corresponding unsaturated compounds.

Halogen is fluorine, chlorine, bromine or iodine. haloalkyl, haloalkenyl and haloalkynyl are alkyl, alkenyl and alkynyl, respectively, which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$. Haloalkoxy is, for example, $OCF_3$, $OCHF_2$, $OCH_2F$, $CF_3CF_2O$, $OCH_2CF_3$ and $OCH_2CH_2Cl$. This applies correspondingly to other halogen-substituted radicals.

A hydrocarbon radical can be an aromatic hydrocarbon radical, such as aryl, or an aliphatic hydrocarbon radical; an aliphatic hydrocarbon radical generally being a straight-chain or branched saturated or unsaturated hydrocarbon radical having preferably 1 to 18, particularly preferably 1 to 12, carbon atoms, for example alkyl, alkenyl or alkynyl.

An aliphatic hydrocarbon radical is preferably alkyl, alkenyl or alkynyl having up to 12 carbon atoms; this applies correspondingly to an aliphatic hydrocarbon radical in a hydrocarbonoxy radical.

A ring is a carbocyclic or heterocyclic, mono-, bi-or polycyclic, unsubstituted or substituted ring system which is saturated, unsaturated or aromatic. Examples of carbocyclic rings are aryl, cycloalkyl or cycloalkenyl.

Aryl is generally a mono-, bi- or polycyclic aromatic hydrocarbon radical having preferably 6–20 carbon atoms, with preference 6 to 14 carbon atoms, particularly preferably 6 to 10 carbon atoms, which may be fused with mono-, bi- or polycyclic, unsubstituted or substituted, aromatic heterocyclyl or mono-, bi- or polycyclic, unsubstituted or substituted, saturated or unsaturated carbocyclyl, for example cycloalkyl or cycloalkenyl, or mono-, bi- or polycyclic, unsubstituted or substituted, saturated or unsaturated heterocyclyl. Examples of aryl radicals are phenyl, naphthyl, tetrahydronaphthyl, indenyl, indanyl, pentalenyl and fluorenyl, particularly preferably phenyl.

A heterocyclic ring, heterocyclic radical or heterocyclyl is a mono-, bi- or polycyclic unsubstituted or substituted ring system which is saturated, unsaturated and/or aromatic and contains one or more, preferably 1 to 4, heteroatoms, preferably from the group consisting of N, S and O.

Preference is given to saturated heterocycles having 3 to 7 ring atoms and one or two heteroatoms from the group consisting of N, O and S, where the chalcogens are not adjacent. Particular preference is given to monocyclic rings having 3 to 7 ring atoms and one heteroatom from the group consisting of N, O and S, and also to morpholine, dioxolane, piperazine, imidazoline and oxazolidine. Very particularly preferred saturated heterocycles are oxirane, pyrrolidone, morpholine and tetrahydrofuran.

Preference is also given to partially unsaturated heterocycles having 5 to 7 ring atoms and one or two heteroatoms from the group consisting of N, O and S. Particular preference is given to partially unsaturated heterocycles having 5 or 6 ring atoms and one heteroatom from the group consisting of N, O and S. Very particularly preferred partially unsaturated heterocycles are pyrazoline, imidazoline and isoxazoline.

Preference is also given to heteroaryl, for example mono- or bicyclic aromatic heterocycles having 5 or 6 ring atoms which contain one to four heteroatoms from the group consisting of N, O and S, where the chalcogens are not adjacent.

Particular preference is given to monocyclic aromatic heterocycles having 5 or 6 ring atoms including one heteroatom from the group consisting of N, O and S, and also to pyrimidine, pyrazine, pyridazine, oxazole, thiazole, thiadiazole, oxadiazole, pyrazole triazole and isoxazole. Very particular preference is given to pyrazole, thiazole, triazole and furan.

Mono- or disubstituted amino is a chemically stable radical from the group of the substituted amino radicals which are N-substituted, for example, by one or two identical or different radicals from the group consisting of alkyl, alkoxy, acyl and aryl; preferably monoalkylamino, dialkylamino, acylamino, arylamino, N-alkyl-N-arylamino and N-heterocycles; here, preference is given to alkyl radicals having 1 to 4 carbon atoms; aryl is preferably phenyl or substituted phenyl; acyl corresponds to the definition given further below and is preferably formyl, $(C_1-C_4)$-alkylcarbonyl or $(C_1-C_4)$-alkylsulfonyl. This applies correspondingly to substituted hydroxylamino or hydrazino.

Unsubstituted or substituted phenyl is preferably phenyl which is unsubstituted or mono- or polysubstituted, preferably up to trisubstituted, in the case of halogen such as Cl and F also up to pentasubstituted, by identical or different radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

The herbicidal compositions according to the invention comprising compounds of the formula (I) and surfactants B) have excellent herbicidal activity and, in a preferred embodiment, superadditive effects. Owing to the improved control of harmful plants by the herbicidal compositions according to the invention, it is possible to reduce the application rate and/or to increase the safety margin. Both make sense, both from an economical and an ecological point of view. The amounts of the components A)+B) to be employed and the ratio of the components A):B) depend on a whole range of factors.

In a preferred embodiment, the herbicidal compositions according to the invention are characterized in that they have a synergistically effective amount of a combination of the compounds of the formula (I) with surfactants B). Here, it has to be emphasized in particular that even in combinations where the application rates or weight ratios of A):B) are such that a synergism cannot be demonstrated clearly in each case—for example owing to the fact that the individual compounds are usually employed in the combination in very different application rates or else because the control of harmful plants by the individual compounds is already very good—a synergistic action is generally inherent to the herbicidal compositions of the invention.

Components A) and B) of the herbicidal compositions according to the invention can be formulated separately and applied by the tank mix method, or they can be contained together in a ready-to-use formulation which can then be applied in a customary manner, for example in the form of a spray liquor.

The herbicidal compositions according to the invention can be formulated in various ways depending on the prevailing biological and/or physical-chemical parameters. Examples of suitable formulation options are: wettable powders (WP), water-soluble powders (SP), water-soluble concentrates (SL), emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), granules for broadcasting and soil application, granules (GR) in the form of microgranules, spray granules, coating granules and adsorption granules, water-dispersable granules (WG), water-soluble granules (SG), ULV formulations, microcapsules and waxes. These individual formulation types are known in principle and are described, for example, in: Winnacker-Küchler, "Chemische Technologie" [Chemical Technology], volume 7, C.Hauser Verlag Munich, 4th edition 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzfl̈achenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th edition 1986.

Based on these formulations it is also possible to produce combinations with other agrochemically active compounds which differ from component A), such as insecticides, acaricides, herbicides, fungicides, safenerns, fertilizers and/or growth regulators, for example in the form of a ready-to-use formulation or as tank mix. Wettable powders are preparations which are uniformly dispersable in water and which contain, in addition to the active compound A) and/or the surfactant B), and in addition to a diluent or inert substance, also surfactants of ionic and/or nonionic nature which are different from surfactant B) (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2′-dinaphthylmethane-6,6′-disulfonate, sodium dibutyinaphthalene sulfonate or else sodium oleoylmethyltaurinate. To prepare the wettable powders, the herbicidally active compounds A) and/or surfactants B) are finely ground, for example in customary apparatus such as hammer mills, fan mills and air-jet mills, and are mixed simultaneously or subsequently with the formulation auxiliaries.

Emsulsifiable concentrates are prepared by dissolving the active compound A) and/or the surfactant B) in an organic solvent, for example butanol, cyclohexanone, dimethylformamide, xylene or else relatively high-boiling aromatic compounds or hydrocarbons or mixtures of the organic solvents with addition of one or more surfactants of ionic and/or nonionic nature differing from surfactant B) (emulsifiers). Suitable for use as emulsifiers are, for example: calcium alkylarylsulfonates, such as calcium dodecylbenzenesulfonate, or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters, or polyoxyethylene sorbitan esters, for example polyoxyethylene sorbitan fatty acid esters.

Water-soluble concentrates are obtained, for example, by dissolving the active compound A) and/or the surfactant B) in water or a water-miscible solvent and adding, if appropriate, further auxiliaries such as water-soluble surfactants.

Dusts are obtained by grinding the active compound A) and/or the surfactant B) with finely divided solid substances, for example talc, natural clays, such as kaolin, bentonite and pyrophyllite, or diatomaceous earth.

Suspension concentrates can be water- or oil-based. They can be prepared, for example, by wet milling using commercially customary bead mills, with or without the addition of surfactants differing from surfactant B), as already mentioned above, for example, in the case of the other formulation types.

Emulsions, for example oil-in-water emulsions (EW) can be prepared, for example, by means of stirrers, colloid mills and/or static mixers using aqueous organic solvents and, if appropriate, surfactants differing from surfactant B), as already mentioned above, for example, in the case of the other formulation types.

Granules can be prepared either by spraying the active compound A) and/or surfactant B) onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds A) and/or surfactants B) can also be granulated in the manner which is customary for the preparation of fertilizer granules—if desired as a mixture with fertilizers.

Water-dispersable granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8–57.

For further details on the formulation of crop protection products, see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

The herbicidal compositions according to the invention generally comprise from 0.01 to 99% by weight, in particular from 0.1 to 95% by weight, of one or more compounds of the formula (I).

In wettable powders, the concentration of active compound is, for example, from about 10 to 90% by weight, the remainder to 100% by weight consisting of customary formulation constituents and, if appropriate, surfactants B). In emulsifiable concentrates, the concentration of active compound can be from about 1 to 90, preferably from 5 to 80,% by weight. Formulations in the form of dusts comprise from 1 to 30% by weight of active compound, preferably most commonly from 5 to 20% by weight of active compound, while sprayable solutions comprise from about 0.05 to 80, preferably from 2 to 50,% by weight of active compound. In the case of water-dispersable granules, the content of active compound depends partly on whether the active compound is in liquid or solid form and on the granulation auxiliaries, fillers, etc., that are used. In water-dispersable granules the content of active compound is, for example, between 1 and 95% by weight, preferably between 10 and 80% by weight.

Suitable further formulation forms are, for example, controlled-release formulations, in particular by incorporating the active compounds into carrier materials. The incorporation of active compounds into carrier materials for providing formulations which allow controlled release is known in principle and can be found in the expert literature. Examples can be found in C. L. Foy, D. W. Pritchard, "Pesticide Formulation and Technology", CRC Press, 1996, page 273 ff. and literature cited therein, and in D. A. Knowles, "Chemistry and Technology of Agrochemical Formulations", Kluwer Academic Press, 1998, page 132 ff. and literature cited therein.

The carrier materials which surround or coat the active compounds are chosen such that they are solid in a suitable temperature range, preferably in a range of about 0–50° C. Solid materials are to be understood as meaning materials which are hard, resilient in a wax-like manner, amorphous or crystalline, but which are not or not yet present in the liquid state. The carrier materials can be of inorganic or organic nature and of synthetic or natural origin.

One possibility of incorporating the agrochemically active compounds into suitable carrier materials is, for example, microencapsulation. These microcapsules can consist of polymeric materials of synthetic and/or natural origin. Examples of suitable materials include polyureas, polyurethanes, polyamides, melamine resins, gelatin, wax and starch.

Microcapsules of some of these materials can be prepared, for example, by the interfacial polycondensation method. Particle size and wall thickness, and thus also the release rates, can be controlled easily via the amount of monomers, the amount of active compound, the amounts of water and solvent and the process parameters.

In the case of microcapsules made of polyurethanes or polyureas, the method that is most frequently employed for constructing the capsule wall mentioned around the active compound to be coated is an interfacial polymerization with oil-in-water emulsions, where the organic phase contains an oil-soluble prepolymer with free isocyanate groups, in addition to the active compound.

Suitable prepolymers are the customary isocyanates known to the person skilled in the art, for example based on toluene 2,4-diisocyanate, toluene 2,6-diisocyanate, methylene bis(phenyl 4-isocyanate) and hexamethylene diisocyanate. The polymerization, i.e. the synthesis of the mantle of the microcapsules, is generally carried out by customary methods known to the person skilled in the art.

The capsule-forming material from which the microcapsule mantles are constructed is preferably obtained from oil-soluble isocyanate group-containing prepolymers, which are a group of industrial mixed products, in each case consisting of polyisocyanates based on condensates of aniline and formaldehyde. These industrial mixed products differ from one another in the degree of condensation and, if appropriate, chemical modifications. For the user, important characteristics are viscosity and the content of free isocyanate groups. Typical commercial products are the Desmodur® brand (Bayer AG) and the Voranate® brand (Dow Chemicals). For the invention, the amount of prepolymer with isocyanate groups used is preferably ≦5% by weight, based on the total formulation; preference is given to 0.5–5% by weight, in particular 1–2% by weight.

The capsule-forming material is formed by curing the isocyanate prepolymer either in the presence of water at 0–95° C., preferably 20–65° C. or, preferably, using the required amount of a dipolyamine.

If the microcapsules are formed using dipolyamines, suitable dipolyamines are, for example, alkylenediamines, dialkylenetriamines and trialkylenetetramines whose carbon chain units comprise between 2 and 8 carbon atoms. Preference is given to hexamethylenediamine. Here, it is possible to use amounts which are stoichiometric to the amount of isocyanate prepolymer used, or, preferably, to use an excess of up to three times, particularly up to two times, the stoichiometric amount.

The literature discloses further methods for preparing microcapsules from polyurethanes or polyurea, which methods are likewise suitable for preparing the microcapsules according to the invention. These methods are listed below.

U.S. Pat. No. 3,577,515 describes how, after introduction of water-soluble polyamines, the droplet surface in such emulsions cures as a result of addition to the prepolymers containing isocyanate groups. This forms a polyurea outer mantle.

U.S. Pat. No. 4,140,516 discloses that, even in the absence of external water-soluble amines, microcapsules having an outer wall of the polyurea type can be produced by permitting partial hydrolysis in the emulsion of the prepolymer bearing isocyanate functions. In the course of this, some of the amino groups are reformed from the isocyanate groups and, as a result of internal polyaddition with subsequent curing, the desired capsule mantle is likewise formed. The use of tolylene disocyanate, hexamethylene diisocyanate, methylenebis(phenyl isocyanate) and of its higher homologues is described. If curing is to be performed using an external polyamine, this usually originates from the group consisting of ethylene diamine, propylene-diamine, hexamethylenediamine, diethylenetriamine and tetraethylenepentamine.

DE-A-2 757 017 discloses internally structured microcapsules whose wall material has the nature of a mixed polymer crosslinked by urea and urethane motifs. The active compound is situated in the interior of the capsule, dissolved in an organic solvent. Typically, to make up the capsule wall here, 10% of prepolymer, based on the total formulation, is required.

The same prepolymer is also used in WO-A-96/09760 to encapsulate, for example, endosulfan.

WO-A-95/23506 discloses endosulfan-charged polyurea microcapsules in which the active compound is present as a cooled melt. As prepolymer, a mixture of methylenebis (phenyl isocyanate) and its higher homologues is described; the amount of prepolymer used is over 6%, based on the total formulation. Curing is performed using a mixture of polyamines.

The content of the patents and patent applications listed above is, with respect to the materials of the microcapsule wall and the preparation processes, an important and integral part of the present invention and is included in the present application by way of reference.

A further possibility of encapsulation is capsule formation using, for example, melamine/formaldehyde or urea/formaldehyde.

To this end, melamine, or the abovementioned isocyanate prepolymers, is/are initially charged in water and admixed with the water-insoluble active compound. Prior to the addition, the active compound has been dispersed or dissolved in a water-insoluble solvent and emulsified. By establishing an acidic pH of about 3–5, preferably about 3–4, and stirring at elevated temperature between 30 and 60° C., preferably 50° C., for several hours, the capsule wall is formed by polycondensation. Examples are described in U.S. Pat. Nos. 4,157,983 and 3,594,328, the content of which, with respect to the preparation of the capsules, is included in the present application by way of reference.

Another suitable method for microencapsulation of the agrochemically active compounds is coacervation. To this end, the water-insoluble agrochemically active compound is dispersed in water and admixed with an anionic water-soluble polymer and a cationic material. The microcapsules formed by coacervation, containing the originally water-soluble polymer as wall material, are water-insoluble. In the last step, the capsule is then cured by condensation with aldehydes. Suitable for this purpose is, for example, the combination gelatin/gum arabic (1:1) and formaldehyde. The process of microencapsulation by coacervation is known to the person skilled in the art. The method is described in detail, for example, in J. A. Bahan "Microencapsulation using Coacervation/Phase Separation Techniques, Controlled Released Technology: Methods Theory and Application", Vol. 2, Kydoniens, A. F, Ed. CRC Press, Inc., Boca Raton, Fla. 1980, Chapter 4.

For microencapsulation, it is finally possible, for example, to emulsify the active compound and the polymer which forms the capsule wall in water using a suitable surfactant. Here, polymer and active compound must not dissolve in each other. The solvent is then evaporated with stirring. When the water is removed, the polymer forms a layer on the surface of the emulsified drop.

Another suitable material for preparing microcapsules is wax. To this end, self-emulsifying waxes are dissolved in water by heating and applying shear forces, or are converted into an emulsion by adding surfactants and heating, whilst applying shear forces. Lipophilic agrochemically active compounds dissolve in molten and emulsified wax. During cooling, the drops solidify, thus forming the wax dispersion.

Alternatively, it is possible to prepare wax dispersions by dispersing active compound/wax extrusion granules in water or oil, followed by fine grinding, for example to particle sizes of <20 μm.

Suitable waxes are, for example, PEG 6000 in a mixture with non-hydrophilic waxes, Synchrowachs HGLC1, Mostermont® CAV2, Hoechst-Wachs OP3 or combinations of these waxes.

An aqueous dispersion of the particles (microcapsules or wax particles) can be obtained similarly to the recipes for a CS formulation (capsule suspension).

The microcapsules obtained by the methods described above can be incorporated into various formulations mentioned above in the text. It is also possible to incorporate further active compounds into the formulation, for example water-soluble active compounds into the aqueous phase of the capsule dispersion, or, for example, solid active compounds into WG formulations.

After microencapsulation, the capsules can be freed from the solvent and dried by customary methods, for example spray drying. In this state, the capsules can be stored and shipped. Prior to application to the crop in question, they are formulated, optionally with further active compounds, adjuvants and the customary additives. However, the dispersion obtained after curing of the capsules can also be used for preparing suitable agrochemical formulations which comprise the abovementioned further components, without isolation of the capsules from the dispersions.

In these microcapsule dispersions, it is possible to use organic solvents or mixtures thereof, from the group of the N-alkyl fatty acid amides, N-alkyllactams, fatty acid esters, cyclohexanones, isophorones, phthalic esters and aromatic hydrocarbons, lower-alkyl-substituted naphthalene derivatives being particularly suitable.

Solvents which are suitable for the purpose of the invention and commercially available are, for example, Solvesso® 200, Solvesso® 150 and Solvesso® 100 (1), butyl diglycol acetate, Shellsol® RA (2), Acetrel® 400 (3), Agsolex® 8 (4), Agsolex® 12 (5), Norpar® 13 (6), Norpar® 15 (7), Isopar® V (8), Exsol® D 100 (9), Shellsol® K (10) and Shellsol® R (11), which are of the following composition:

(1) Mixtures of aromatic compounds; manufacturer: Exxon.
(2) Mixtures of alkylated benzenes, boiling range 183–312° C., manufacturer: Shell.
(3) High-boiling mixture of aromatic compounds, boiling range: 332–355° C., manufacturer: Exxon.
(4) N-Octylpyrrolidone, boiling point (0.3 mmHg) 100° C., manufacturer: GAF.
(5) N-Dodecylpyrrolidone, boiling point (0.3 mmHg) 145° C., manufacturer: GAF.
(6) Aliphatic hydrocarbons, boiling range: 228–243° C., manufacturer: Exxon.
(7) Aliphatic hydrocarbons, boiling range: 252–272° C., manufacturer: Exxon.
(8) Aliphatic hydrocarbons, boiling range: 278–305° C., manufacturer: Exxon.
(9) Aliphatic hydrocarbons, boiling range: 233–263° C., manufacturer: Exxon.
(10) Aliphatic hydrocarbons, boiling range: 192–254° C., manufacturer: Shell.
(11) Aliphatic hydrocarbons, boiling range: 203–267° C., manufacturer: Shell.

Also suitable are mixtures of these solvents with one another. Particularly suitable are butyl diglycol acetate, Acetrel® 400, Agsolex® 8 and Agsolex® 12. Particular preference is given to Solvesso® 200.

The aqueous phase of the dispersions according to the invention contains surface-active formulation auxiliaries from the group of the emulsifiers and dispersants. They originate from a group which comprises, for example, the compound families of the polyvinyl alcohols, the polyalkylene oxides, the condensates of formaldehyde with naphthalenesulfonic acids and/or phenols, the polyacrylates, the copolymers of maleic anhydride with alkylene alkyl ether, the lignosulfonates, and the polyvinylpyrrolidones. These substances are employed in an amount of from 0.2 to 10% by weight, preferably from 0.5 to 4% by weight, based in each case on the total dispersion.

In the case of polyalkylene oxides, preference is given to block copolymers whose molecular center and molecular periphery are formed by a polypropylene oxide block and polyethylene oxide blocks, respectively. Here, particular preference is given to substances in which the polypropylene oxide block has a molar mass of 2 000–3 000 and the percentage of the polyethylene oxide blocks is 60 to 80% of the total molar mass. Such a substance is available, for example, from BASF Wyandotte under the name Pluronic® F87.

Further suitable dispersants are calcium lignosulfonate, highly refined sodium lignosulfonate (for example Vanisperse® CB from Borregaard), dispersant S and dispersant SS from Clariant GmbH, naphthalene/sulfonic acid/formaldehyde condensate sodium salt (for example Morwet® D 425 from Witco or Tamol® NN 8906 from BASF), sodium polycarboxylate (for example Sopropan® T 36 from Rhodia GmbH).

Suitable polyvinyl alcohols are prepared by partial hydrolysis of polyvinyl acetate. They have a degree of hydrolysis of from 72 to 99 mol % and a viscosity of from 2 to 18 cP (measured in 4% strength aqueous solution at 20° C., in accordance with DIN 53 015). Preference is given to using partially hydrolyzed polyvinyl alcohols having a degree of hydrolysis of from 83 to 88 mol % and low viscosity, in particular from 3 to 5 cP.

If appropriate, the aqueous phase of the dispersions comprises at least one further formulation auxiliary from the group of the wetting agents, the antifreeze agents, the thickeners, the preservatives and viscosity-increasing components.

Suitable wetting agents are, for example, representatives from the substance groups of the alkylated naphthalenesulfonic acids, the N-fatty acyl N-alkyl taurides, the fatty acylamidoalkylbetaines, the alkyl polyglycosides, the alpha-olefinsulfonates, the alkylbenzenesulfonates, the esters of sulfosuccinic acid and the fatty alkyl sulfates (which may be modified by alkyleneoxy groups). Here, the percentage is between 0 and 5% by weight, preferably between 0 and 2% by weight, based on the total formulation.

Suitable commercial products are, for example, Darvan® No. 3, Vanisperse® CB, Hoe S1728 (Clariant GmbH), Luviskol® K 30, Reserve C, Forianit® P, Sokalan® CP 10, Maranil A, Genapol® PF 40, Genapol® LRO, tributylphenol polyglycol ether, such as the Sapogenat T brands (Clariant GmbH), nonylphenol polyglycol ether, such as the Arkopal® N brands (Clariant GmbH) or tristyrylphenol polyglycol ether derivatives.

Preservatives which may be added to the aqueous dispersions are the following agents: formaldehyde or hexahydrotriazine derivatives, such as, for example, Mergal® KM 200 from Riedel de Haen or Cobate® C from Rhone Poulenc, isothiazolinone derivatives, such as, for example, Mergal® K9N from Riedel de Haen or Kathon® CG from Rohm and Haas, 1,2-benzisothiazolin-2-ones, such as, for example, Nipacide® BIT 20 from Nipa Laboratorien GmbH or Mergal® K10 from Riedel de Haen or 5-bromo-5-nitro-1,3-dioxane (Bronidox® LK from Henkel). The percentage of these preservatives is at most 2% by weight, based on the total formulation.

Suitable antifreeze agents are, for example, mono- or polyhydric alcohols, glycol ethers or urea, in particular calcium chloride, glycerol, isopropanol, propylene glycol monomethyl ether, di- or tripropylene glycol monomethyl ether or cyclohexanol. The percentage of these antifreeze agents is at most 20% by weight, based on the total dispersion.

Thickeners may be of inorganic or organic nature; they can also be combined. Suitable thickeners are, for example, those based on alumosilicate, xanthane, methylcellulose, polysaccharide, alkaline earth metal silicate, gelatin and polyvinyl alcohol, such as, for example, Bentone® EW, Vegum®, Rodopole 23 or Kelzan® S. Their percentage is 0–0.5% by weight, preferably 0.3% by weight, based on the total dispersion.

The invention also relates to a process for preparing the microcapsule dispersions according to the invention, which comprises initially preparing a crude preemulsion of organic and aqueous phases (without diamine) and then subjecting this preemulsion to shear forces by passing it through a mixer, which preferably operates continuously, for example a static mixer, a toothed colloid mill or the like. Only in this step is the fineness required for later microcapsule formation of the emulsified oil droplets achieved. Finally, if appropriate after addition of a diamine, the entire substance volume is cured by polyreaction. Alternatively, the addition of water-soluble polyamine is dispensed with, and the finished emulsion is stirred for a certain period of time at a suitable temperature, for example for 6 h at 70° C.

For preparing a controlled release combination it is also possible, instead of microencapsulation, to introduce the active compound into an organic matrix, such as, for example, wax. It is also possible to use inorganic matrices, for example silicates, alumosilicates or aluminum oxides or minerals based on these abovementioned materials. Incorporation into such an organic or inorganic matrix results in physical binding of the agrochemically active compounds.

Possible release mechanisms are, for example, abiotic and/or biotic degradation (weathering), bursting of the matrix or the capsule walls, or diffusion or dissolution of the active compound from the matrix or the capsules. This may take place depending on the contact with liquids, for example water, or depending on the temperature.

In general, the major amount of active compound is released from the matrix or the microcapsules within the first 4 weeks after application, preferably within the first 7 days.

In addition, said formulations of active compound may comprise the auxiliaries such as tackifiers, wetting agents, dispersants, emulsifiers, penetrants, preservatives, antifreeze agents, solvents, fillers, carriers, colorants, antifoams, adjuvants such as mineral or vegetable oils and derivatives thereof, evaporation inhibitors and pH and viscosity regulators which are customary in each case.

The herbicidal compositions according to the invention can be prepared by customary processes, for example by mixing the components with the aid of stirrers, shakers or (static) mixers.

In a preferred embodiment of this invention, the formulations comprising compounds of the formula (I) are mixed in the spray tank with surfactants B) and/or formulations thereof. To this end, the compounds of the formula (I) can be formulated, for example on the basis of kaolin, as water-dispersible granules, where the content of compounds of the formula (I) may vary within wide limits between 0.01 and 99% by weight, preferably between 0.5 and 80% by weight. In addition to the compounds of the formula (I), these formulations may comprise further agrochemically active compounds, such as safeners, for example in an amount of from 0.1 to 50% by weight, preferably from 0.5 to 40% by weight. The surfactants B) can be added as pure substances or in formulated form, preferably as a liquid product, such as a water-soluble concentrate or an emulsifiable concentrate.

Ready-to-use formulations can be obtained by preparing, for example, aqueous concentrates, aqueous dispersions, emulsifiable concentrates or oil dispersions of compounds of the formula (I), surfactants B) and further auxiliaries. In the ready-to-use formulations, the amount of compounds of the formula (I) can vary within wide limits and is generally between 0.01 and 99% by weight, preferably between 0.1 and 60% by weight. The amount of surfactants B) can also vary within wide limits and is generally between 1 and 80% by weight, as a rule between 5 and 50% by weight. Finally, the ready-to-use formulations may also comprise further agrochemically active compounds such as safeners, for example in an amount of from 0.01 to 60% by weight, preferably from 0.1 to 40% by weight.

If appropriate, the formulations may comprise auxiliaries such as solvents, for example aromatic solvents, such as xylenes or mixtures of aromatic compounds from the Solvesso® series such as Solvesso® 100, Solvesso® 150 or Solvesso® 200 from Exxon; aliphatic or isoparaffinic solvents, such as products from the Exxol®-D or Isopur® series from Exxon; oils of vegetable, mineral or animal origin and derivatives thereof, such as rapeseed oils or rapeseed oil methyl esters; esters, such as butyl acetate; ethers, such as diethyl ether, THF or dioxane. The solvent content is preferably 1–95% by weight, particularly preferably 5–80% by weight. Further suitable auxiliaries are, for example, emulsifiers (preferred content: 0.1–10% by weight), dispersants (preferred content: 0.1–10% by weight) and thickeners (preferred content: 0.1–5% by weight), and, if appropriate, stabilizers, such as antifoams, agents for reducing drift, fertilizers, for example nitrogen-containing fertilizers, water scavengers, acid scavengers and crystallization inhibitors.

The herbicidal compositions according to the invention can be used pre- or post-emergence, preferably post-emergence, for example by spraying. The use of the mixtures allows the amount of preparation required for controlling weeds to be reduced considerably.

The surfactants B) to be used according to the invention are generally applied together with the compound(s) A) or immediately afterward, preferably in the form of a spray liquor which comprises effective amounts of surfactants B) and compounds A) and, if appropriate, further customary auxiliaries. The spray liquor is preferably prepared based on water and/or an oil, for example a high-boiling hydrocarbon such as kerosene or paraffin. Here, the herbicidal compositions according to the invention can be realized as a tank mix or via a "ready-to-use formulation".

The weight ratio of compounds A) to surfactant B) can vary within a wide range and depends, for example, on the efficacy of the herbicide. It is generally in a range of from 10:1 to 1:5000, preferably from 4:1 to 1:2000.

The application rates of the compound(s) of the formula (I) are generally between 10 and 2000 g of AS/ha (AS= active substance, i.e. application rate based on the active compound), preferably between 50 and 1000 g of AS/ha. The application rates of surfactants B) are generally between 1 and 5000 g of surfactant/ha; preference is given to from 10 to 2000 g of surfactant/ha, in particular from 50 to 1000 g of surfactant/ha.

The concentration of the surfactants B) to be used according to the invention in a spray liquor is generally from 0.05 to 4% by weight, preferably 0.1 to 1% by weight, in particular from 0.1 to 0.3% by weight, of surfactant.

The herbicidal compositions according to the invention may, as additional components, also comprise agrochemically active compounds different from component A), such as herbicides, fungicides, insecticides or safeners.

The herbicidally active compounds which are present in the herbicidal compositions according to the invention are, for example, ALS inhibitors (acetolactate synthetase inhibitors) or herbicides other than ALS inhibitors, such as herbicides from the group of the carbamates, thiocarbamates, haloacetanilides, substituted phenoxy-, naphthoxy- and phenoxyphenoxycarboxylic acid derivatives and heteroaryloxyphenoxyalkanecarboxylic acid derivatives such as quinolyloxy-, quinoxalyloxy-, pyridyloxy-, benzoxazolyloxy- and benzothiazolyloxyphenoxyalkanecarboxylic acid esters, cyclohexanedione derivatives, imidazolinones, phosphorus-containing herbicides, for example of the glufosinate type or the glyphosate type, pyrimidinyloxypyridinecarboxylic acid derivatives, pyrimidyloxybenzoic acid derivatives, triazolopyrimidinesulfonamide derivates and S-(N-aryl-N-alkylcarbamoylmethyl)dithiophosphoric acid esters.

Preferred ALS inhibitors are from the series of the sulfonylureas and/or their salts, for example pyrimidinyl- or triazinylaminocarbonyl[benzene-, pyridine-, pyrazole-, thiophene- and (alkylsulfonyl)alkylamino]sulfamides. Preferred as substituents on the pyrimidine ring or triazine ring are alkoxy, alkyl, haloalkoxy, haloalkyl, halogen or dimethylamino, it being possible for all substituents to be combined independently of one another. Preferred substituents in the benzene-, pyridine-, pyrazole-, thiophene- or (alkylsulfonyl)alkylamino moiety are alkyl, alkoxy, halogen, amino, alkylamino, dialkylamino, nitro, alkoxycarbonyl, aminocarbonyl, alkylaminocarbonyl, dialkylaminocarbonyl, alkoxyaminocarbonyl, haloalkoxy, haloalkyl, alkylcarbonyl, alkoxyalkyl, (alkanesulfonyl)alkylamino. Examples of such suitable sulfonylureas are A1) Phenyl- and benzylsulfonylureas and related compounds, for example
1-(2-chlorophenylsulfonyl)-3-(4-methoxy-6-methyl-1,3,5-triazin-2-yl)urea (chlorsulfuron),
1-(2-ethoxycarbonylphenylsulfonyl)-3-(4-chloro-6-methoxypyrimidin-2-yl)urea (chlorimuron-ethyl),
1-(2-methoxyphenylsulfonyl)-3-(4-methoxy-6-methyl-1,3,5-triazin-2-yl)urea (metsulfuron-methyl),
1-(2-chloroethoxyphenylsulfonyl)-3-(4-methoxy-6-methyl-1,3,5-triazin-2-yl)urea (triasulfuron),
1-(2-methoxycarbonylphenylsulfonyl)-3-(4,6-dimethylpyrimidin-2-yl)urea (sulfumeturon-methyl),
1-(2-methoxycarbonylphenylsulfonyl)-3-(4-methoxy-6-methyl-1,3,5-triazin-2-yl)-3-methylurea (tribenuron-methyl),
1-(2-methoxycarbonylbenzylsulfonyl)-3-(4,6-dimethoxypyrimidin-2-yl)urea (bensulfuron-methyl),
1-(2-methoxycarbonylphenylsulfonyl)-3-(4,6-bis-(difluoromethoxy)pyrimidin-2-yl)urea, (primisulfuron-methyl),
3-(4-ethyl-6-methoxy-1,3,5-triazin-2-yl)-1-(2,3-dihydro-1,1-dioxo-2-methylbenzo-[b]thiophen-7-sulfonyl)urea (EP-A 0 079 683),
3-(4-ethoxy-6-ethyl-1,3,5-triazin-2-yl)-1-(2,3-dihydro-1,1-dioxo-2-methylbenzo[b]-thiophen-7-sulfonyl)urea (EP-A 0 790 683),
3-(4-methoxy-6-methyl-1,3,5-triazin-2-yl)-1-(2-methoxycarbonyl-5-iodophenyl-sulfonyl)urea (iodosulfuron-methyl and its sodium salt, WO 92/13845),
DPX-66037, triflusulfuron-methyl (see Brighton Crop Prot. Conf.—Weeds—1995, p.853),
CGA-277476, (see Brighton Crop Prot. Conf.—Weeds—1995, p. 79),
methyl 2-[3-(4,6-dimethoxypyrimidin-2-yl)ureidosulfonyl]-4-methanesulfonamidomethylbenzoate (mesosulfuron-methyl, WO 95/10507),
N,N-dimethyl-2-[3-(4,6-dimethoxypyrimidin-2-yl)ureidosulfonyl]4-formylaminobenzamide (foramsulfuron, WO 95/01344);
A2) Thienylsulfonylureas, for example
1-(2-methoxycarbonylthiophen-3-yl)-3-(4-methoxy-6-methyl-1,3,5-triazin-2-yl)urea (thifensulfuron-methyl);
A3) Pyrazolylsulfonylureas, for example
1-(4-ethoxycarbonyl-1-methylpyrazol-5-yl-sulfonyl)-3-(4,6-dimethoxypyrimidin-2-yl)urea (pyrazosulfuron-methyl);
methyl 3-chloro-5-(4,6-dimethoxypyrimidin-2-yl-carbamoylsulfamoyl)-1-methylpyrazole-4-carboxylate (EP-A 0 282 613);
methyl 5-(4,6-dimethylpyrimidin-2-yl-carbamoylsulfamoyl)-1-(2-pyridyl)pyrazole-4-carboxylate (NC-330, see Brighton Crop Prot. Conference 'Weeds' 1991, Vol.1, p. 45 et seq.),
DPX-A8947, azimsulfuron, (see Brighton Crop Prot. Conf. 'Weeds' 1995, p. 65);

A4) Sulfone diamide derivatives, for example
3-(4,6-dimethoxypyrimidin-2-yl)-1-(N-methyl-N-methylsulfonylaminosulfonyl)urea (amidosulfuron) and its structural analogs (EP-A0 131 258 and Z. Pfl. Krankh. Pfl. Schutz, Special Issue XII, 489–497 (1990));

A5) Pyridylsulfonylureas, for example
1-(3-N,N-dimethylaminocarbonylpyridin-2-ylsulfonyl)-3-(4,6-dimethoxypyrimid in-2-yl)urea (nicosulfuron),
1-(3-ethylsulfonylpyridin-2-ylsulfonyl)-3-(-(4,6-dimethoxypyrimidin-2-yl)urea (rimsulfuron),
methyl 2-[3-(4,6-dimethoxypyrimidin-2-yl)ureidosulfonyl]-6-trifluoromethyl-3-pyridinecarboxylate, sodium salt (DPX-KE 459, flupyrsulfuron, see Brighton Crop Prot. Conf. Weeds, 1995, p. 49), pyridylsulfonylureas as are described, for example, in DE-A 40 00 503 and DE-A 40 30 577, preferably those of the formula

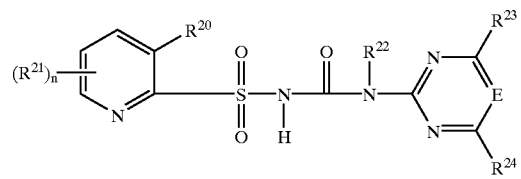

in which

E is CH or N, preferably CH, $R^{20}$ is iodine or $NR^{25}R^{26}$, $R^{21}$ is hydrogen, halogen, cyano, $(C_1-C_3)$alkyl, $(C_1-C_3)$alkoxy, $(C_1-C_3)$haloalkyl, $(C_1-C_3)$haloalkoxy, $(C_1-C_3)$alkylthio, $(C_1-C_3)$alkoxy$(C_1-C_3)$alkyl, $(C_1-C_3)$-alkoxycarbonyl, mono- or di($(C_1-C_3)$alkyl)amino, $(C_1-C_3)$alkylsulfinyl or sulfonyl, $SO_2-NR^xR^y$ or $CO-NR^xR^y$, in particular hydrogen, $R^x$, $R^y$ independently of one another are hydrogen, $(C_1-C_3)$alkyl, $(C_1-C_3)$alkenyl, $(C_1-C_3)$alkynyl or together are $-(CH_2)_4-$, $-(CH_2)_5-$ or $-(CH_2)_2-O-(CH_2)_2-$, n is 0, 1, 2 or 3, preferably 0 or 1, $R^{22}$ is hydrogen or $CH_3$, $R^{23}$ is halogen, $(C_1-C_2)$alkyl, $(C_1-C_2)$alkoxy, $(C_1-C_2)$haloalkyl, in particular $CF_3$, $(C_1-C_2)$haloalkoxy, preferably $OCHF_2$ or $OCH_2CF_3$, $R^{24}$ is $(C_1-C_2)$alkyl, $(C_1-C_2)$haloalkoxy, preferably $OCHF_2$, or $(C_1-C_2)$alkoxy, $R^{25}$ is $(C_1-C_4)$alkyl, $R^{26}$ is $(C_1-C_4)$alkylsulfonyl or $R^{25}$ and $R^{26}$ together are a chain of the formula $-(CH_2)_3SO_2-$ or $-(CH_2)_4SO_2-$, for example 3-(4,6-dimethoxypyrimiden-2-yl)-1-(3-N-methylsulfonyl-N-methylaminopyridin-2-yl)sulfonylurea, or their salts;

A6) Alkoxyphenoxysulfonylureas as are described, for example, in EP-A 0 342 569, preferably those of the formula

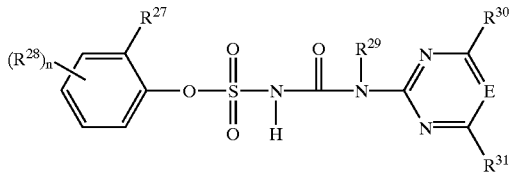

in which
E is CH or N, preferably CH,
$R^{27}$ is ethoxy, propoxy or isopropoxy,
$R^{28}$ is halogen, $NO_2$, $CF_3$, CN, $(C_1-C_4)$alkyl, $(C_1-C_4)$ alkoxy, $(C_1-C_4)$alkylthio or $(C_1-C_3)$alkoxycarbonyl, preferably in the 6-position on the phenyl ring,
n is 0, 1, 2 or 3, preferably 0 or 1,
$R^{29}$ is hydrogen, $(C_1-C_4)$alkyl or $(C_3-C_4)$alkenyl,
$R^{30}$, $R^{31}$ independently of one another are halogen, $(C_1-C_2)$ alkyl, $(C_1-C_2)$alkoxy, $(C_1-C_2)$haloalkyl, $(C_1-C_2)$ haloalkoxy or $(C_1-C_2)$alkoxy$(C_1-C_2)$alkyl, preferably $OCH_3$ or $CH_3$, for example 3-(4,6-dimethoxypyrimidin-2-yl)-1-(2-ethoxyphenoxy)sulfonylurea, or their salts;
A7) Imidazolylsulfonylureas, for example
MON 37500, sulfosulfuron (see Brighton Crop Prot. Conf. 'Weeds', 1995, p. 57), and other related sulfonylurea derivatives and mixtures of these.

Typical representatives of these active substances are, inter alia, the compounds listed hereinbelow: amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, halosulfuron-methyl, imazosulfuron, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, triflusulfuron-methyl, iodosulfuron-methyl and its sodium salt (WO 92/13845), mesosulfuron-methyl and its sodium salt (Agrow No. 347, Mar. 3, 2000, page 22 (PJB Publications Ltd. 2000)) and foramsulfuron and its sodium salt (Agrow No.338, Oct. 15, 1999, page 26 (PJB Publications Ltd. 2000)).

The active substances listed hereinabove are known, for example, from C. D. S. Tomlin, "The Pesticide Manual", $12^{th}$ Edition (1999), The British Crop Protection Council, or the references cited after the individual active substances.

The herbicidal active substances which are present in the herbicidal compositions according to the invention and which differ from the ALS inhibitors are, for example, herbicides from the group of the carbamates, thiocarbamates, haloacetanilides, substituted phenoxy-, naphthoxy- and phenoxyphenoxycarboxylic acid derivatives, and heteroaryloxyphenoxyalkanecarboxylic acid derivatives such as quinolyloxy-, quinoxalyloxy-, pyridyloxy-, benzoxazolyloxy- and benzothiazolyloxyphenoxyalkanecarboxylic esters, cyclohexanedione derivatives, imidazolinones, phosphorus-containing herbicides, for example of the glufosinate type or of the glyphosate type, pyrimidinyloxypyridinecarboxylic acid derivatives, pyrimidyloxybenzoic acid derivatives, triazolopyrimidinesulfonamide derivatives and S-(N-aryl-N-alkylcarbamoylmethyl) dithiophosphoric esters. Preferred in this context are phenoxyphenoxy- and heteroaryloxyphenoxycarboxylic acid esters and salts, imidazolinones and herbicides such as bentazone, cyanazine, atrazine, dicamba or hydroxybenzonitriles such as bromoxynil and ioxynil and other foliar-acting herbicides.

Suitable herbicidal active substances A) which may be present as component A) in the herbicidal compositions according to the invention and which differ from ALS inhibitors are, for example:

B) Herbicides of the phenoxyphenoxy- and heteroaryloxyphenoxycarboxylic acid derivatives type, such as
B1) Phenoxyphenoxy- and benzyloxyphenoxycarboxylic acid derivatives, for example methyl 2-(4-(2,4-dichlorophenoxy)phenoxy)propionate (diclofop-methyl),
methyl 2-(4-(4-bromo-2-chlorophenoxy)phenoxy) propionate (DE-A 26 01 548),
methyl 2-(4-(4-bromo-2-fluorophenoxy)phenoxy) propionate (U.S. Pat. No. 4,808,750),
methyl 2-(4-(2-chloro-4-trifluoromethylphenoxy)phenoxy) propionate (DE-A 24 33 067),
methyl 2-(4-(2-fluoro-4-trifluoromethylphenoxy)phenoxy) propionate (U.S. Pat. No. 4,808,750),
methyl 2-(4-(2,4-dichlorobenzyl)phenoxy)propionate (DE-A 24 17 487), ethyl 4-(4-(4-trifluoromethylphenoxy) phenoxy)pent-2-enoate, methyl 2-(4-(4-trifluoromethylphenoxy)phenoxy)propionate (DE-A 24 33 067);
B2) "Mononuclear" heteroaryloxyphenoxyalkanecarboxylic acid derivatives, for example
ethyl 2-(4-(3,5-dichloropyridyl-2-oxy)phenoxy)propionate (EP-A 0 002 925),
propargyl 2-(4-(3,5-dichloropyridyl-2-oxy)phenoxy) propionate (EP-A 0 003 114),
methyl 2-(4-(3-chloro-5-trifluoromethyl-2-pyridyloxy) phenoxy)propionate (EP-A 0 003 890),
ethyl 2-(4-(3-chloro-5-trifluoromethyl-2-pyridyloxy) phenoxy)propionate (EP-A 0 003 890),
propargyl 2-(4-(5-chloro-3-fluoro-2-pyridyloxy)phenoxy) propionate (EP-A 0 191 736),
butyl 2-(4-(5-trifluoromethyl-2-pyridyloxy)phenoxy) propionate (fluazifop-butyl);
B3) "Binuclear" heteroaryloxyphenoxyalkanecarboxylic acid derivatives, for example
methyl and ethyl 2-(4-(6-chloro-2-quinoxalyloxy)phenoxy) propionates (quizalofopmethyl and quizalofopethyl),
methyl 2-(4-(6-fluoro-2-quinoxalyloxy)phenoxy)propionate (see J. Pest. Sci. Vol. 10, 61 (1985)),
2-isopropylideneaminooxyethyl 2-(4-(6-chloro-2-quinoxalyloxy)phenoxy)propionate (propaquizafop),
ethyl 2-(4-(6-chlorobenzoxazol-2-yloxy)phenoxy) propionate (fenoxaprop-ethyl), its D(+) isomer (fenoxaprop-P-ethyl) and ethyl 2-(4-(6-chlorobenzthiazol-2-yloxy)phenoxy)propionate (DE-A 26 40 730),
tetrahydro-2-furylmethyl 2-(4-(6-chloroquinoxalyloxy) phenoxy)propionate (EP-A 0 323 727);
C) Chloroacetanilides, for example
N-methoxymethyl-2,6-diethylchloroacetanilide (alachlor),
N-(3-methoxyprop-2-yl)-2-methyl-6-ethylchloroacetanilide (metolachlor),
2,6-dimethyl-N-(3-methyl-1,2,4-oxadiazol-5-ylmethyl) chloroacetanilide,
N-(2,6-dimethylphenyl)-N-(1-pyrazolylmethyl) chloroacetamide (metazachlor);
D) Thiocarbamates, for example
S-ethyl N,N-dipropylthiocarbamate (EPTC),
S-ethyl N, N-diisobutylthiocarbamate (butylate);
E) Cyclohexanedione oximes, for example
methyl 3-(1-allyloxyiminobutyl)-4-hydroxy-6,6-dimethyl-2-oxocyclohex-3-enecarboxylate (alloxydim),
2-(1-ethoxyiminobutyl)-5-(2-ethylthiopropyl)-3-hydroxycyclohex-2-en-1-one (sethoxydim),
2-(1-ethoxyiminobutyl)-5-(2-phenylthiopropyl)-3-hydroxycyclohex-2-en-1-one (cloproxydim),
2-(1-(3-chloroallyloxy)iminobutyl)-5-(2-ethylthiopropyl)-3-hydroxycyclohex-2-en-1-one,
2-(1-(3-chloroallyloxy)iminopropyl)-5-(2-ethylthiopropyl)-3-hydroxycyclohex-2-en-1-one (clethodim), 2-(1-ethoxyiminobutyl)-3-hydroxy-5-(thian-3-yl)-cyclohex-2-enone (cycloxydim),
2-(1-ethoxyiminopropyl)-5-(2,4,6-trimethylphenyl)-3-hydroxycyclohex-2-en-1-one (tralkoxydim);

F) Imidazolinones, for example
methyl 2-(4-isopropyl-4-methyl-5-oxo-2-imidazolin-2-yl)-5-methylbenzoate and 2-(4-isopropyl-4-methyl-5-oxo-2-imidazolin-2-yl)-4-methylbenzoic acid (imazamethabenz),
5-ethyl-2-(4-isopropyl-4-methyl-5-oxo-2-imidazolin-2-yl)pyridine-3-carboxylic acid (imazethapyr),
2-(4-isopropyl-4-methyl-5-oxo-2-imidazolin-2-yl)quinoline-3-carboxylic acid (imazaquin),
2-(4-isopropyl-4-methyl-5-oxo-2-imidazolin-2-yl)pyridine-3-carboxylic acid (imazapyr),
5-methyl-2-(4-isopropyl-4-methyl-5-oxo-2-imidazolin-2-yl)pyridine-3-carboxylic acid (imazethamethapyr);

G) Triazolopyrimidinesulfonamide derivatives, for example
N-(2,6-difluorophenyl)-7-methyl-1,2,4-triazolo[1,5-c]pyrimidine-2-sulfonamide (flumetsulam),
N-(2,6-dichloro-3-methylphenyl)-5,7-dimethoxy-1,2,4-triazolo[1,5-c]pyrimidine-2-sulfonamide,
N-(2,6-difluorophenyl)-7-fluoro-5-methoxy-1,2,4-triazolo[1,5-c]pyrimidine-2-sulfonamide,
N-(2,6-dichloro-3-methylphenyl)-7-chloro-5-methoxy-1,2,4-triazolo[1,5-c]pyrimidine-2-sulfonamide,
N-(2-chloro-6-methoxycarbonyl)-5,7-dimethyl-1,2,4-triazolo[1,5-c]pyrimidine-2-sulfonamide (EP-A 0 343 752, US-A 4,988,812);

H) Benzoylcyclohexanediones, for example
2-(2-chloro-4-methylsulfonylbenzoyl)cyclohexane-1,3-dione (SC-0051, EP-A 0 137 963), 2-(2-nitrobenzoyl)-4,4-dimethylcyclohexane-1,3-dione (EP-A 0 274 634),
2-(2-nitro-3-methylsulfonylbenzoyl)-4,4-dimethylcyclohexane-1,3-dione (WO 91/13548);

I) Pyrimidinyloxypyridinecarboxylic acid and pyrimidinyloxybenzoic acid derivatives, for example
benzyl 3-(4,6-dimethoxypyrimidin-2-yl)oxypyridine-2-carboxylate (EP-A 0 249 707),
methyl 3-(4,6-dimethoxypyrimidin-2-yl)oxypyridine-2-carboxylate (EP-A 0 249 707),
2,6-bis[(4,6-dimethoxypyrimidin-2-yl)oxy]benzoic acid (EP-A 0 321 846),
1-(ethoxycarbonyloxyethyl) 2,6-bis[(4,6-dimethoxypyrimidin-2-yl)oxy]benzoate (EP-A 0 472 113);

J) S-(N-Aryl-N-alkylcarbamoylmethyl) dithiophosphonates such as S-[N-(4-chlorophenyl)-N-isopropylcarbamoylmethyl]O,O-dimethyl dithiophosphate (anilophos);

K) Alkylazines, for example as described in WO-A 97/08156, WO-A-97/31904, DE-A-1 9826670, WO-A-98/15536, WO-A-98/15537, WO-A-98/15538, WO-A-98/15539 and also DE-A-1 9828519, WO-A-98/34925, WO-A-98/42684, WO-A-99/18100, WO-A-99/19309, WO-A-99/37627 and WO-A-99/65882, preferably those of the formula (E)

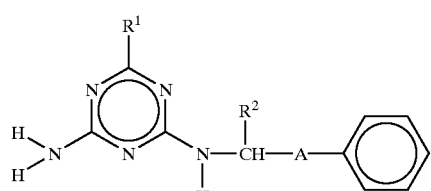

(E)

in which $R^1$ is $(C_1-C_4)$alkyl or $(C_1-C_4)$haloalkyl;
$R^2$ is $(C_1-C_4)$alkyl, $(C_3-C_6)$cycloalkyl or $(C_3-C_6)$cycloalkyl-$(C_1-C_4)$alkyl and
A is —$CH_2$—, —$CH_2$—$CH_2$—, —$CH_2$—$CH_2$—$CH_2$—, —O—, —$CH_2$—$CH_2$—O—, —$CH_2$—$CH_2$—$CH_2$—O—, especially preferably those of the formulae E1-E7

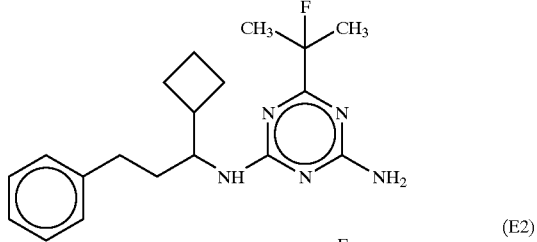

(E1)

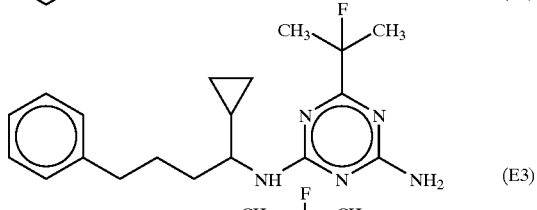

(E2)

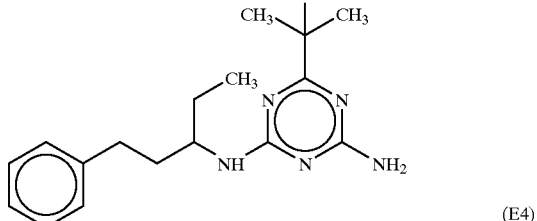

(E3)

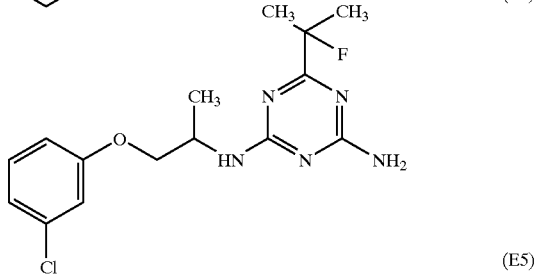

(E4)

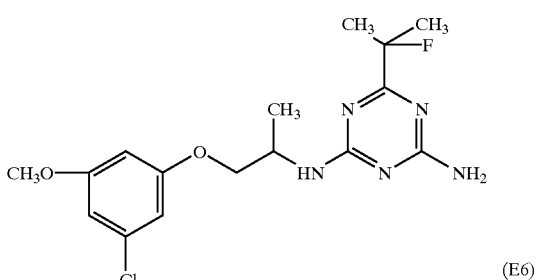

(E5)

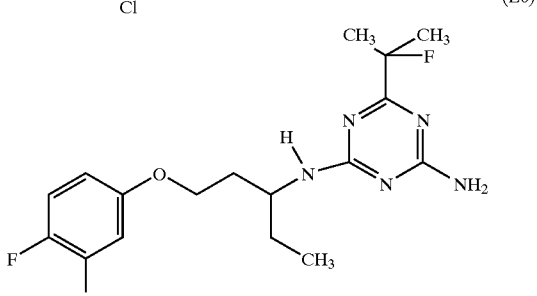

(E6)

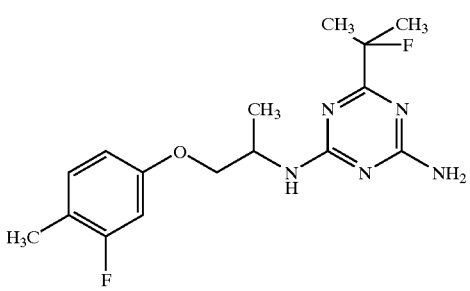

(E7)

L) Phosphorus-containing herbicides, for example of the glufosinate type, such as glufosinate in the narrow sense, i.e. D,L-2-amino4-[hydroxy(methyl)phosphinyl]-butanoic acid, glufosinatemonoammonium salts, L-glufosinate, L- or (2S)-2-amino-4-[hydroxy(methyl)phosphinyl]butanoic acid, L-glufosinatemonoammonium salt or bialaphos (or bilanafos), i.e. L-2-amino-4-[hydroxy(methyl)phosphinyl] butanoyl-L-alanyl-L-alanine, in particular its sodium salt, or of the glyphosate type, such as glyphosate, i.e. N-(phosphonomethyl)glycine, glyphosatemonoisopropylammonium salt, glyphosate sodium salt, or sulfosate, i.e. N-(phosphonomethyl)glycine trimesium salt=N-(phosphonomethyl)glycine trimethylsulfoxonium salt.

The herbicides of groups B to L are known, for example, from each of the specifications stated above and from "The Pesticide Manual", 12$^{th}$ Edition, 1999, The British Crop Protection Council, "Agricultural Chemicals Book II—Herbicides—", by W. T. Thompson, Thompson Publications, Fresno Calif., USA 1990 and "Farm Chemicals Handbook '90", Meister Publishing Company, Willoughby Ohio, USA, 1990.

The herbicidal compositions according to the invention have excellent herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the herbicidal compositions according to the invention, without this being a restriction to certain species.

Examples of weed species on which the active compounds act efficiently are, from amongst the monocotyledons, Avena, Lolium, Alopecurus, Phalaris, Echinochloa, Digitaria, Setaria and also Cyperus species from the annual sector and, from amongst the perennial species, Agropyron, Cynodon, Imperata and Sorghum, and also perennial Cyperus species.

In the case of the dicotyledonous weed species, the spectrum of action extends to species such as, for example, Galium, Viola, Veronica, Lamium, Stellaria, Amaranthus, Sinapis, lpomoea, Matricaria, Abutilon and Sida from amongst the annuals, and Convolvulus, Cirsium, Rumex and Artemisia in the case of the perennial weeds.

The compositions according to the invention also effect outstanding control of harmful plants which occur under the specific conditions of rice-growing such as, for example, Echinochloa, Sagittaria, Alisma, Eleocharis, Scirpus and Cyperus.

If the herbicidal compositions according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the herbicidal compositions according to the invention are applied post-emergence to the green parts of the plants, growth also stops drastically a very short time after the treatment and the weed plants remain at the developmental stage of the point in time of application, or they die completely after a certain time, so that in this manner competition from the weeds, which is harmful to the crop plants, is eliminated at a very early point in time and in a sustained manner.

Although the herbicidal compositions according to the invention have an excellent herbicidal activity against monocotyledonous and dicotyledonous weeds, in particular against dicotyledonous weeds, crop plants of economically important crops, for example dicotyledonous crops such as soya, cotton, oilseed rape, sugar beet, in particular soya, or gramineous crops such as wheat, barley, rye, rice or corn, are not damaged at all, or only to a negligible extent. For these reasons, the present compounds are highly suitable for selectively controlling undesired plant growth in plantings of agriculturally useful plants or of ornamental plants.

In addition, the herbicidal compositions according to the invention have outstanding growth-regulating properties in crop plants. They engage in the plant metabolism in a regulating manner and can thus be employed for the targeted control of plant constituents and for facilitating harvesting, such as for example by provoking desiccation and stunted growth. Furthermore, they are also suitable for generally regulating and inhibiting undesirable vegetative growth, without destroying the plants in the process. Inhibition of vegetative growth plays an important role in many monocotyledonous and dicotyledonous crops because lodging can be reduced hereby, or prevented completely.

Owing to their herbicidal and plant-growth-regulatory properties, the herbicidal compositions according to the invention can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage stability, composition and to specific ingredients of the harvested product. Thus, transgenic plants having an increased starch content or a modified quality of the starch or those having a different fatty acid composition of the harvested product are known.

The use of the compositions according to the invention in economically important transgenic crops of useful and ornamental plants, for example of cereals, such as wheat, barley, rye, oats, millet, rice, manioc and corn, or else in crops of sugar beet, cotton, soya, oilseed rape, potatoes, tomatoes, peas and other vegetable species is preferred. The compositions according to the invention can preferably be used as herbicides in crops of useful plants which are resistant or which have been made resistant by genetic engineering toward the phytotoxic effects of the herbicides.

When using the herbicidal compositions according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crop is resistant, and an effect on the growth and the yield of the transgenic crop plants.

The invention therefore also provides for the use of the compositions according to the invention as herbicides for controlling harmful plants, preferably in crop plants, where the crop plants may also be transgenic crop plants, for example bromoxynil-tolerant cotton.

The herbicidal compositions according to the invention can also be used in a non-selective manner for controlling undesirable vegetation, for example on paths, open spaces, industrial sites or rail tracks. Owing to the relatively low application rate of the herbicidal compositions according to the invention, they are, as a rule, already well tolerated. In particular, the combinations according to the invention lead to a reduction in the absolute application rate in comparison with the individual application of a herbicidal active compound.

If, if desired, the tolerance and/or selectivity of the herbicidal compositions according to the invention are to be increased further, it may be advantageous to apply them jointly as a mixture or staggered in time one after the other together with safeners or antidotes.

Compounds which are suitable as safeners or antidotes for the herbicidal compositions according to the invention are disclosed, for example, in EP-A-333 131 (ZA-89/1960), EP-A-269 806 (U.S. Pat. No. 4,891,057), EP-A-346 620 (AU-A-89/34951) and the international patent applications PCTIEP 90/01966 (WO-91108202) and PCT/EP 90102020 (WO-911078474) and the literature cited therein or can be prepared by the processes described therein. Other suitable safeners are known from EP-A-94 349 (U.S. Pat. No. 4,902,304), EP-A-191 736 (U.S. Pat. No. 4,881,966) and EP-A-0 492 366 and the literature cited therein.

In a preferred embodiment, the herbicidal compositions of the present invention therefore additionally comprise C) one or more compounds which act as safeners or antidotes.

Preferred antidotes or safeners or groups of compounds which are suitable as safeners or antidotes in the herbicidal compositions of the invention are, inter alia:

a) Compounds of the dichlorophenylpyrazoline-3-carboxylic acid type, preferably compounds such as ethyl 1-(2,4-dichlorophenyl)-5-(ethoxycarbonyl)-5-methyl-2-pyrazoline-3-carboxylate (compound Cl-1, mefenpyr-diethyl) and related compounds as they are described in the international application WO 91/07874 (PCT/EP 90102020);

b) Dichlorophenylpyrazolecarboxylic acid derivatives, preferably compounds such as ethyl 1-(2,4-dichlorophenyl)-5-methylpyrazole-3-carboxylate (compound Cl-2), ethyl 1-(2,4-dichlorophenyl)-5-isopropylpyrazole-3-carboxylate (compound $C_1$–3), ethyl 1-(2,4-dichlorophenyl)-5-(1,1-dimethylethyl)pyrazole-3-carboxylate (compound $C_1$–4), ethyl 1-(2,4-dichlorophenyl)-5-phenylpyrazole-3-carboxylate (compound $C_1$–5) and related compounds as are described in EP-A-0 333 131 and EP-A-0 269 806;

c) Compounds of the triazolecarboxylic acid type, preferably compounds such as ethyl 1-(2,4-dichlorophenyl)-5-trichloromethyl-(1H)-1,2,4-triazole-3-carboxylate (compound Cl–6, fenchlorazole-ethyl) and related compounds (see EP-A-0 174 562 and EP-A-0 346 620);

d) Compounds of the dichlorobenzyl-2-isoxazoline-3-carboxylic acid type, compounds of the 5-benzyl- or 5-phenyl-2-isoxazoline-3-carboxylic acid type, preferably compounds such as ethyl 5-(2,4-dichlorobenzyl)-2-isoxazoline-3-carboxylate (compound C1–7) or ethyl 5-phenyl-2-isoxazoline-3-carboxylate (compound C1–8) and related compounds as they are described in the international patent application WO 91/08202 (PCT/EP 90/01966);

e) Compounds of the 8-quinolinoxyacetic acid type, preferably compounds such as 1-methylhex-1-yl 5-chloro-8-quinolinoxyacetate (cloquintocet-mexyl, C2–1), 1,3-dimethylbut-1-yl 5-chloro-8-quinolinoxyacetate (C2–2), 4-allyloxybutyl 5-chloro-8-quinolinoxyacetate (C2–3), 1-allyloxyprop-2-yl 5-chloro-8-quinolinoxyacetate (C2–4), ethyl 5-chloro-8-quinolinoxyacetate (C2–5), methyl 5-chloro-8-quinolinoxyacetate (C2–6), allyl 5-chloro-8-quinolinoxyacetate (C2–7), 2-(2-propylidene-iminooxy)-1-ethyl 5-chloro-8-quinolinoxyacetate (C2–8), 2-oxoprop-1-yl 5-chloro-8-quinolinoxyacetate (C2–9) and related compounds as they are described in EP-A-0 086 750, EP-A-0 094 349 and EP-A-0 191 736 or EP-A-0 492 366;

f) Compounds of the 5-chloro-8-quinolinoxymalonic acid type, preferably compounds such as diethyl 5-chloro-8-quinolinoxymalonate, diallyl 5-chloro-8-quinolinoxymalonate, methyl ethyl 5-chloro-8-quinolinoxymalonate and related compounds as they have been described and proposed in the German patent application EP-A-0 582 198;

g) Active compounds of the type of the phenoxyacetic- or -propionic acid derivatives or of the aromatic carboxylic acids, such as, for example, 2,4-dichlorophenoxyacetic acid (and its esters) (2,4-D), 4-chloro-2-methylphenoxypropionic ester (mecoprop), MCPA or 3,6-dichloro-2-methoxybenzoic acid (and its esters) (dicamba);

h) Compounds of the 5,5-diphenyl-2-isoxazoline-3-carboxylic acid type, preferably ethyl 5,5-diphenyl-2-isoxazoline-3-carboxylate (C3–1, isoxadifen-ethyl);

i) Compounds known as safeners, for example for rice, such as fenclorim (=4,6-dichloro-2-phenylpyrimidine, Pesticide Manual, 12th Edition, 1999, pp. 386/387), dimepiperate (=S-(1-methyl-1-phenylethyl) 1-piperidinecarbothioate, Pesticide Manual, 12th Editions 1999, pp. 302/303), daimuron (=1-(1-methyl-1-phenylethyl)-3-p-tolylurea, Pesticide Manual, 12th Edition, 1999, p. 247), cumyluron (=3-(2-chlorophenylmethyl)-1-(1-methyl-1-phenyl-ethyl)urea, JP-A-60/087254), methoxyphenone (=3,3'-dimethyl-4-methoxybenzophenone), CSB (=1-bromo-4-(chloromethylsulfonyl)benzene, CAS Reg. No. 54091-06-4).

In addition, at least some of the compounds mentioned are described in EP-A-0 640 587, which is herewith referred to for publication purposes.

j) A further important group of compounds which are suitable as safeners and antidotes is disclosed in WO 95107897.

The safeners (antidotes) of the above groups a) to j) reduce or contain phytotoxic effects which may occur in crops of useful plants when employing the herbicidal compositions according to the invention without adversely affecting the efficacy of the herbicides against harmful plants. This allows the field of application of the herbicidal compositions according to the invention to be widened considerably, and, in particular, the use of safeners allows combinations to be employed whose use has previously only been possible with limitations or with insufficient success, i.e. combinations which, without safeners, had a poor spectrum of action and led to insufficient control of harmful plants when applied at low dosage rates.

The herbicidal compositions according to the invention and the abovementioned safeners can be applied together (as a ready-to-use formulation or by the tank mix method) or in succession in an arbitrary sequence. The weight ratio of safener:herbicide (compound(s) of the formula (I) and/or the salts thereof) may vary within wide limits and is preferably in the range of 1:100 to 100:1, in particular 1:10 to 10:1. The amounts of herbicide(s) and safener(s) which are optimal in each case depend usually on the type of the herbicidal composition and/or on the safener used and on the nature of the plant stand to be treated.

Depending on their properties, the safeners of type C) may be used for pretreating the seed of the crop plant (seed dressing) or incorporated into the seed furrow prior to sowing or applied together with the herbicide mix before or after emergence of the plants.

The pre-emergence treatment includes not only the treatment of the area under cultivation before sowing, but also the treatment of the areas under cultivation where seed has been sown but the plants have not yet emerged. The joint application together with the herbicide mix is preferred. To this end, tank mixes or ready-to-use formulations may be employed.

The required application rates of the safeners may vary within wide limits, depending on the indication and the herbicide used, and are, as a rule, in the range of 0.001 to 1 kg, preferably 0.005 to 0.2 kg, of active compound per hectare.

The present invention also relates to a method of controlling undesired plants, preferably in crop plants, which comprises applying a herbicidally active amount of the herbicidal composition according to the invention, for example to the plants, the parts of the plants, the seeds of the plants or the area under cultivation.

In a preferred variant of the method the herbicidal compositions according to the invention are applied in the form of tank mixes, the individual components, for example in the form of formulations, jointly being mixed in the tank with water or an oil and the resulting spray liquor being applied. Since the crop plant tolerance of the combinations according to the invention is decidedly good while simultaneously effecting very good control of the harmful plants, the combinations can be considered as selective. In a preferred modification of the method, herbicidal compositions are therefore employed for the selective control of undesired plants.

The herbicidal compositions can be applied in the customary manner, for example with water and/or oil as carrier in amounts of approximately 0.5–4000, preferably 100 to 1000, liters of spray liquor/ha. The compositions may also be applied by the low-volume and ultra-low-volume (ULV) methods and in the form of granules and microgranules.

A preferred application relates to the use of herbicidal compositions which comprise components A) and B) in a synergistically effective amount.

The invention also includes herbicidal compositions which comprise mixtures of one or more combination partners A), preferably A1, A2, A3, A4, A5, A6, A7, A8, A9 and/or A10 and one or more combination partners B), if appropriate in combination with one or more safeners C).

Preferred examples of the herbicidal compositions according to the invention which may be mentioned are the following combinations of A1, A2, A3, A4, A5, A6, A7, A8, A9 and/or A10 with surfactants B), without the combinations being limited to those mentioned explicitly:

A1 in combination with one of the surfactants of group B1 to B65 (see Table 1)
A2 in combination with one of the surfactants of group B1 to B65 (see Table 1)
A3 in combination with one of the surfactants of group B1 to B65 (see Table 1)
A4 in combination with one of the surfactants of group B1 to B65 (see Table 1)
A5 in combination with one of the surfactants of group B1 to B65 (see Table 1)
A6 in combination with one of the surfactants of group B1 to B65 (see Table 1)
A7 in combination with one of the surfactants of group B1 to B65 (see Table 1)
A8 in combination with one of the surfactants of group B1 to B65 (see Table 1)
A9 in combination with one of the surfactants of group B1 to B65 (see Table 1)
A10 in combination with one of the surfactants of group B1 to B65 (see Table 1)
A11 in combination with one of the surfactants of group B1 to B65 (see Table 1)
A12 in combination with one of the surfactants of group B1 to B65 (see Table 1)

In addition, the herbicidal compositions of the present invention may comprise, to round off the properties, additionally, in most cases in minor amounts, one, two or more agrochemically active compounds differing from component A) (for example herbicides, insecticides or fungicides).

Thus, there are numerous possibilities of combining a plurality of active compounds with one another and using them jointly for controlling harmful plants, preferably in crop plants, without deviating from the essence of the invention.

To summarize, it can be said that, when compounds of the formula (I) are used together with one or more surfactants B), an excellent herbicidal activity is obtained. The activity of the herbicidal compositions according to the invention in a preferred embodiment is more pronounced than the activity of the individual components employed when used on their own. These effects permit, inter alia, a reduction of the application rate, the control of a broader spectrum of broad-leafed weeds and weed grasses, the closure of activity gaps, also with respect to resistant species, a more rapid and safer action, a complete control of the harmful plants with only one or a few applications, and a widening of the period of use.

The abovementioned properties are needed in practical control of weeds to keep agricultural crops free of undesirable competing plants and thus to secure and/or increase the quality and quantity of the yields. With respect to the described properties, the prior art is considerably surpassed by these novel combinations. In addition, the combinations according to the invention permit, in an excellent manner, the control of harmful plants which are otherwise resistant.

EXAMPLES

Formulation Example 1

An example of a combination according to the invention of compounds of the formula (I) with surfactants is an SL formulation which comprises 5% bromoxynil-potassium, 10% Genapol®-X-150, 84.8% of water and 0.2% of Biozid Mirgal® A. This is obtained by introducing the substances successively with stirring into water. In an analogous manner, it is possible to prepare formulations with other surfactants, where the ratio of active compound/surfactant may vary within wide ranges.

Formulation Example 2

In a 1 l four-necked flask, an aqueous phase comprising 57.9% by weight of water, 5.0% by weight of Atlox® Metasperse 550 S, 1.0% by weight of polyethylene glycol (molecular weight: 4000), 5.0% by weight of Emulsogen® EL 400 and 0.1% by weight of Rhodorsil® 432 is stirred at 60° C. An organic phase comprising 11.1% by weight of bromoxynil-octanoate, 10.0% by weight of Solvesso® 200 and 1.0% by weight of Voranate® M 220 is likewise heated to 60° C. and introduced with vigorous stirring (300 rpm) into the aqueous phase. The mixture is then sheared at a high rotational speed (1500–2000 rpm) until the desired particle size is obtained (up to 1 minute) and then stirred at a rotational speed of about 50–100 rpm for another 6 hours. This gives a microcapsule suspension (CS) having an average capsule diameter of 2–20 micrometers.

Biological Examples

Seeds or rhizome pieces of monocotyledonous and dicotyledonous weeds were placed in sandy loam soil in plastic pots, covered with soil and grown in a greenhouse under good growth conditions. Three weeks after seeding, the test plants were treated in the three-leaf stage. The compositions of the invention, formulated as wettable powders or as emulsion concentrates, were sprayed onto the green parts of the plants at various application rates of 600–800 l of water/ha (converted). The test plants were allowed to stand in the greenhouse under optimum growth conditions for about 3 to 4 weeks, and the effect of the preparations was then rated visually in comparison to untreated controls. The compositions according to the invention have good herbicidal activity against harmful plants of economic importance. The activity of bromoxynil-Na (300 g/ha) in combination with a surfactant such as Genapol® X 150, Genapol® X 200, Sapogenat® T130, Sapogenat® T 200, Sapogenat® T 300, Sapogenat® T 400, Sapogenat® T 500 or Genapol® O 200 at application rates of, for example, 50 g/ha, 100 g/ha, 300 g/ha and 60 g/ha is, for example, considerably higher than, for example, bromoxynil-Na applied with a surfactant having a lower content of ethylene oxide units, such as Genapol® 060 (6 ethylene oxide units).

Bromoxynil-octanoate (300 g of AS/ha and 600 g of AS/ha), formulated according to Formulation Example 2 as a microcapsule suspension (10%) and applied together with a surfactant such as Genapol® X 150, Genapol® X 200, Sapogenat® T130, Sapogenat® T 200, Sapogenat® T 300, Sapogenat® T 400, Sapogenat® T 500 or Genapol® O 200 at application rates of 150 g of surfactant/ha, 300 g of surfactant/ha and 600 g of surfactant/ha showed a herbicidal activity which was considerably higher than a commercial formulation of bromoxynil-octanoate.

What is claimed is:

1. A herbicidal composition, comprising
   A) one or more compounds of the formula (I)

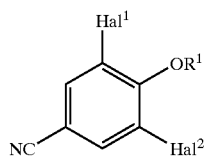

(I)

wherein
   $Hal^1$ and $Hal^2$ are identical or different halogen atoms,
   $R^1$ is H, a cation or a $C_1-C_{20}$-carbon-containing radical, wherein said one or more compounds are microencapsulated into one or more polymeric materials of synthetic and/or natural origin, and
   B) one or more surfactants, comprising as structural element at least 12 alkylene oxide units.

2. The herbicidal composition as claimed in claim 1, comprising as component B) one or more surfactants of the formula (II)

$R^\gamma-(EO)_x(PO)_y(EO)_z-R^\delta$ (II)

in which
   EO is an ethylene oxide unit,
   PO is a propylene oxide unit,
   x is an integer from 0 to 50,
   y is an integer from 0 to 50,
   z is an integer from 0 to 50,
where the sum $(x+y+z) \geq 12$ and $\leq 150$, and
   $R^\gamma$ is OH, an unsubstituted or substituted $C_1-C_{40}$-hydrocarbonoxy radical, an O-acyl radical or NR'R" or $[NR'R''R''']^\oplus X^\ominus$, where R', R", and R''' are identical or different and are H or an unsubstituted or substituted $C_1-C_{30}$-hydrocarbon radical which may be attached via a group $(EO)_w$, where w is an integer of from 1 to 50, and where $X^\ominus$ is an anion, and
   $R^\delta$ is H, an unsubstituted or substituted $C_1-C_{40}$-hydrocarbon radical, an acyl radical or NR'R" or $[NR'R''R''']^\oplus X^\ominus$, where R', R" and R''' are identical or different and are H or an unsubstituted or substituted $C_1-C_{30}$-hydrocarbon radical which may be attached via a group $(EO)_w$, where w is an integer from 1 to 50, and where $X^\oplus$ is an anion.

3. The herbicidal composition as claimed in claim 1, which additionally comprises one or more further components from the group consisting of agrochemically active compounds of a different type and formulation auxiliaries and additives customary in crop protection.

4. A method for controlling harmful plants, which comprises applying the herbicidal composition defined according to claim 1 by the pre-emergence method, the post-emergence method or the pre- and postemergence method to the plants, parts of plants, plant seeds or the area under cultivation.

5. The method as claimed in claim 4 for the selective control of harmful plants in crop plants.

6. The use of the herbicidal composition defined in claim 1 for controlling harmful plants.

7. A process for preparing a herbicidal composition defined according to claim 1, which comprises (a) mixing said one or more compounds of the formula (I) with the one or more polymeric materials thereby forming microcapsules, and (b) adding one or more surfactants B).

8. The process as claimed in claim 7, wherein the components A) and B) as defined in claim 1 are mixed by a tank mix method with water and/or an oil.

9. The herbicidal composition according to claim 1, wherein the microcapsule-forming polymeric material is selected from the group consisting of polyureas, poylurethanes, polyamides, melamin resins, gelatin, wax and starch.

* * * * *